(12) United States Patent
Errico et al.

(10) Patent No.: US 9,149,614 B2
(45) Date of Patent: Oct. 6, 2015

(54) SYSTEMS AND METHODS FOR TREATMENT OF OBESITY AND TYPE 2 DIABETES

(71) Applicants: Joseph P. Errico, Warren, NJ (US); John T. Raffle, Austin, TX (US); Jonathan David Gardiner, Budd Lake, NJ (US)

(72) Inventors: Joseph P. Errico, Warren, NJ (US); John T. Raffle, Austin, TX (US); Jonathan David Gardiner, Budd Lake, NJ (US)

(73) Assignee: E2, LLC, Short Hills, NJ (US)

( * ) Notice: Subject to any disclaimer, the term of this patent is extended or adjusted under 35 U.S.C. 154(b) by 0 days.

(21) Appl. No.: 14/042,654

(22) Filed: Sep. 30, 2013

(65) Prior Publication Data

US 2014/0031738 A1    Jan. 30, 2014

Related U.S. Application Data

(60) Division of application No. 12/836,862, filed on Jul. 15, 2010, now Pat. No. 8,574,184, which is a continuation-in-part of application No. 12/702,469, filed on Feb. 9, 2010, now abandoned, which is a (Continued)

(51) Int. Cl.
*A61F 2/04* (2013.01)
*A61M 27/00* (2006.01)
*A61F 5/00* (2006.01)

(52) U.S. Cl.
CPC ............... *A61M 27/002* (2013.01); *A61F 2/04* (2013.01); *A61F 5/0076* (2013.01); *A61F 2002/044* (2013.01)

(58) Field of Classification Search
CPC ............... A61F 2/02; A61F 2/04; A61F 9/00; A61F 9/007; A61F 27/00
See application file for complete search history.

(56) References Cited

U.S. PATENT DOCUMENTS

| | | |
|---|---|---|
| 5,820,584 A | 10/1998 | Crabb |
| 2004/0092892 A1 | 5/2004 | Kagan et al. |
| 2005/0096750 A1 | 5/2005 | Kagan et al. |
| 2005/0192614 A1 | 9/2005 | Binmoeller |
| 2005/0192629 A1 | 9/2005 | Saadat et al. |
| 2006/0116736 A1 | 6/2006 | DiLorenzo |
| 2008/0103604 A1 | 5/2008 | Levine et al. |

(Continued)

OTHER PUBLICATIONS
PCT International Search Report and Written Opinion dated Feb. 7, 2011 in related PCT Appliction No. PCT/US10/56789 filed Nov. 16, 2010.

(Continued)

*Primary Examiner* — Melanie Hand
(74) *Attorney, Agent, or Firm* — Dentons US LLP

(57) ABSTRACT

The present invention provides systems and methods for treating and controlling obesity and/or type II diabetes. In one aspect of the invention, a device comprises a hollow sleeve sized and shaped for positioning within a duodenum of the patient, an anchor coupled to the proximal end of the sleeve and being sized and shaped to inhibit distal migration of the sleeve and a plurality of elastomeric objects coupled to the distal end of the sleeve and being sized and shaped to inhibit proximal migration of the sleeve through a pylorus of the patient. The bypass device can be placed and removed endoscopically through the patient's esophagus in a minimally invasive outpatient procedure and it is "self-anchoring" and does not require invasive tissue fixation within the patient's GI tract, thereby reducing collateral tissue damage and minimizing its impact on the digestive process.

18 Claims, 32 Drawing Sheets

Related U.S. Application Data continuation-in-part of application No. 12/702,422, filed on Feb. 9, 2010, now Pat. No. 8,475,401, and a continuation-in-part of application No. 12/622,532, filed on Nov. 20, 2009, now abandoned, and a continuation-in-part of application No. 12/622,575, filed on Nov. 20, 2009, now Pat. No. 8,403,877, said application No. 12/622,532 is a continuation-in-part of application No. 12/566,131, filed on Sep. 24, 2009, now abandoned, said application No. 12/622,575 is a continuation-in-part of application No. 12/566,131, said application No. 12/622,532 is a continuation-in-part of application No. 12/566,163, filed on Sep. 24, 2009, now abandoned, said application No. 12/622,575 is a continuation-in-part of application No. 12/566,163, said application No. 12/622,532 is a continuation-in-part of application No. 12/566,193, filed on Sep. 24, 2009, now abandoned, said application No. 12/622,575 is a continuation-in-part of application No. 12/566,193, said application No. 12/566,131 is a continuation-in-part of application No. 12/508,701, filed on Jul. 27, 2009, now abandoned, said application No. 12/566,163 is a continuation-in-part of application No. 12/508,701, said application No. 12/566,193 is a continuation-in-part of application No. 12/508,701.

(60) Provisional application No. 61/239,506, filed on Sep. 3, 2009, provisional application No. 61/222,206, filed on Jul. 1, 2009.

(56) References Cited

U.S. PATENT DOCUMENTS

| | | |
|---|---|---|
| 2008/0262520 A1 | 10/2008 | Makower et al. |
| 2008/0287969 A1 | 11/2008 | Tsonton et al. |
| 2009/0198210 A1 | 8/2009 | Burnett et al. |
| 2009/0247992 A1 | 10/2009 | Shalon et al. |
| 2009/0259237 A1 | 10/2009 | Grau et al. |

OTHER PUBLICATIONS

PCT International Search Report and Written Opionion dated Jan. 5, 2011 in related PCT Application No. PCT/US10/55765 filed Nov. 8, 2010.

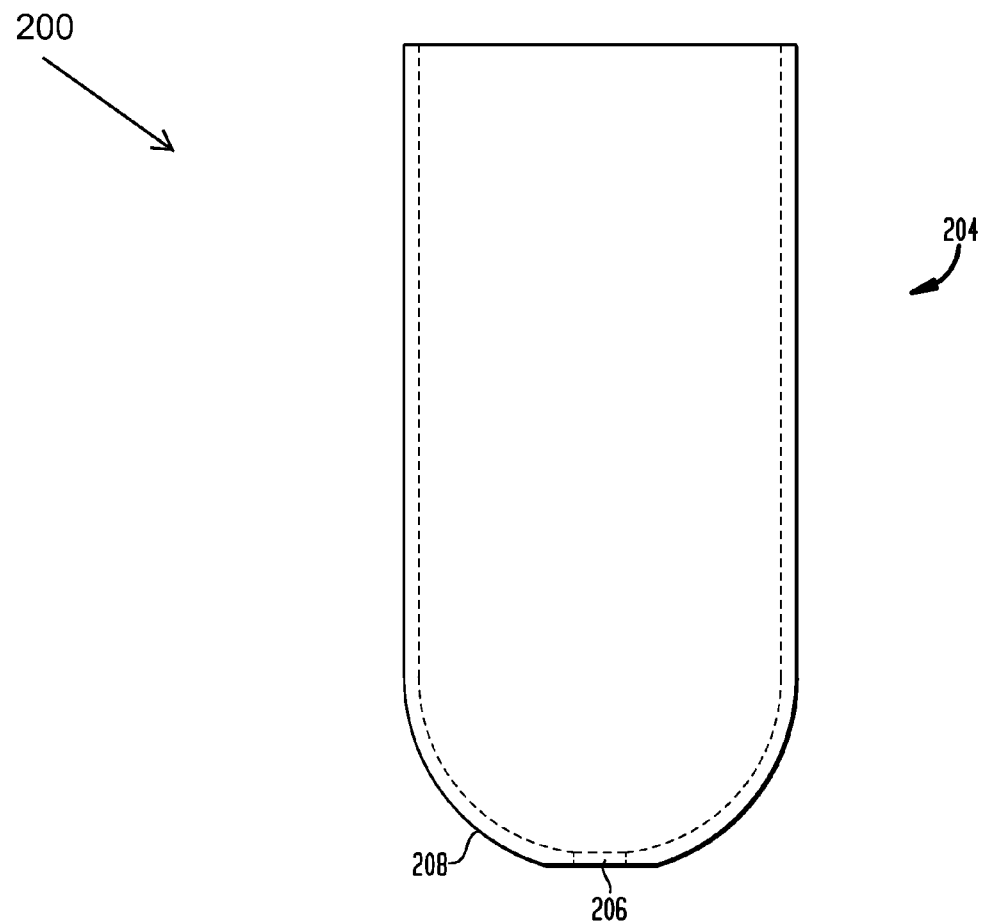

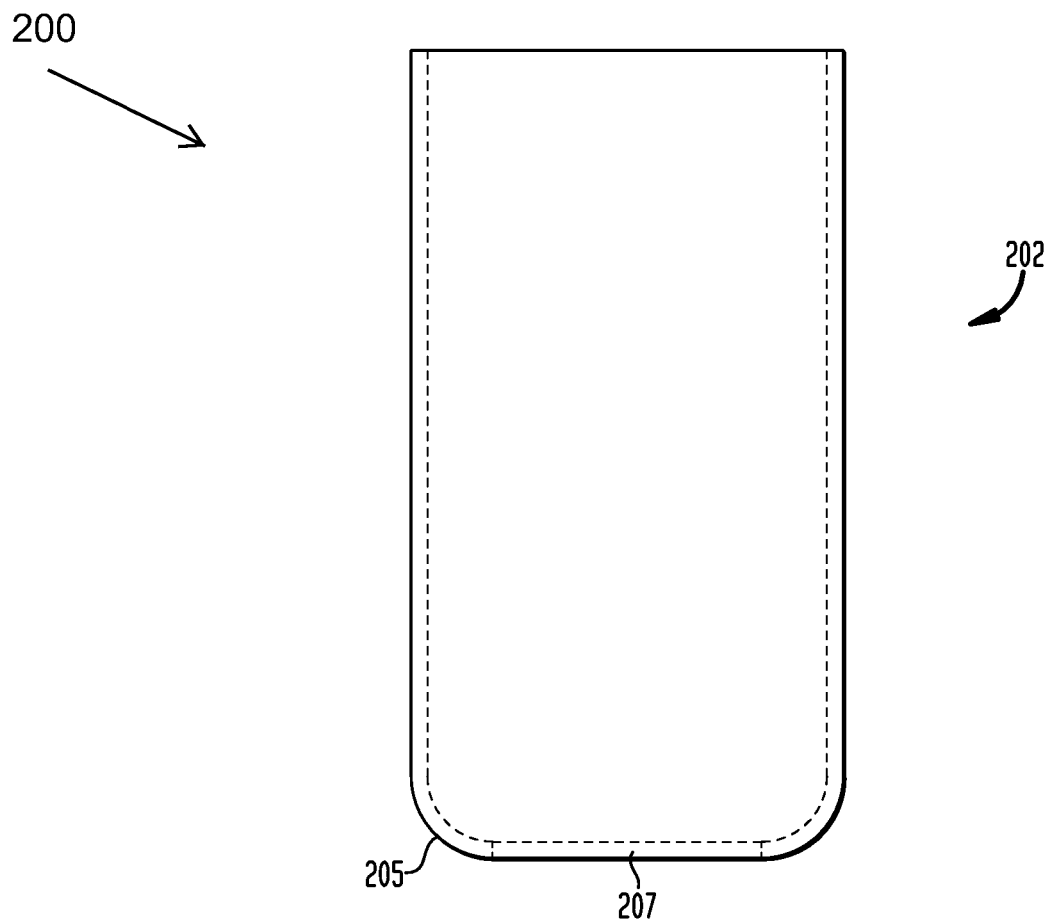

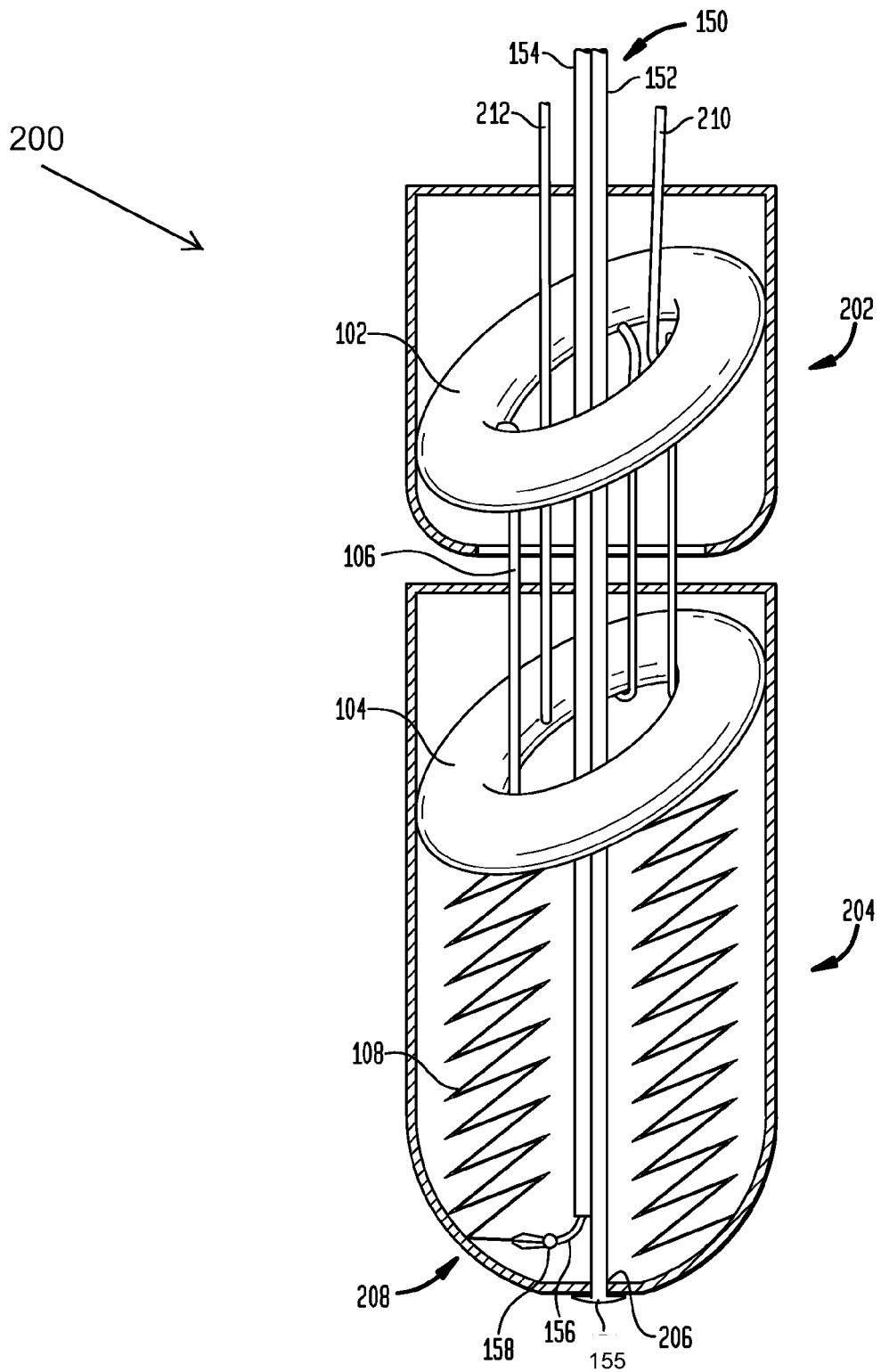

FIG. 19
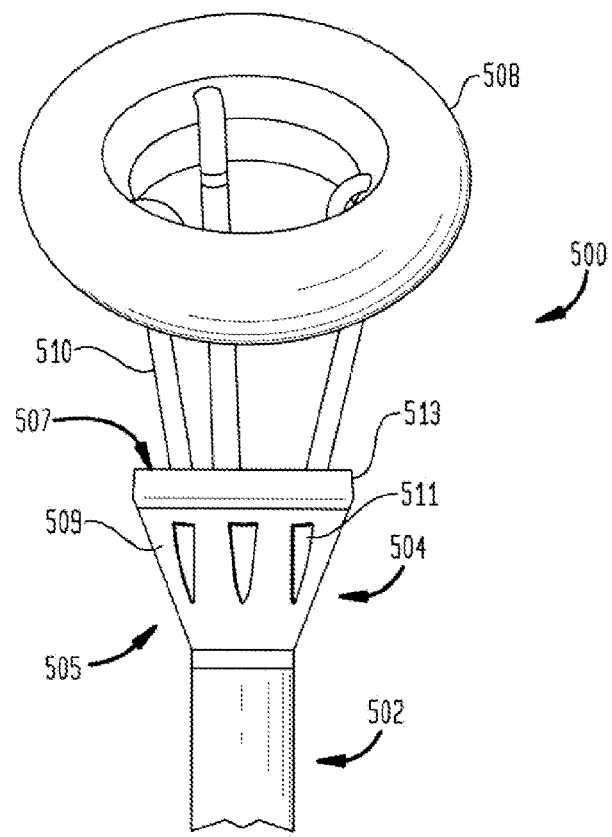
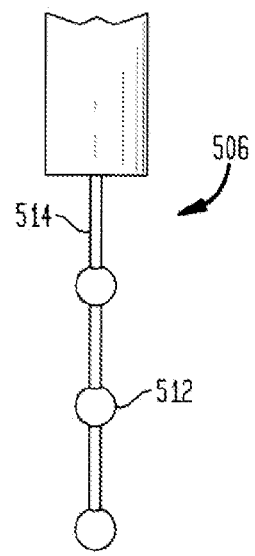

SYSTEMS AND METHODS FOR TREATMENT OF OBESITY AND TYPE 2 DIABETES

CROSS REFERENCE TO RELATED APPLICATIONS

This application is a divisional application of U.S. patent application Ser. No. 12/836,862 filed Jul. 15, 2010 which is a continuation-in-part of U.S. patent application Ser. No. 12/702,469 filed Feb. 9, 2010. U.S. patent application Ser. No. 12/702,469 is a continuation-in-part of U.S. patent application Ser. No. 12/702,422 filed Feb. 9, 2010. U.S. patent application Ser. No. 12/702,469 is a continuation-in-part of US of U.S. patent application Ser. No. 12/622,532 filed Nov. 20, 2009 and Ser. No. 12/622,575 filed Nov. 20, 2009, both of which are a continuation-in-part of U.S. patent application Ser. No. 12/566,131, filed Sep. 24, 2009; Ser. No. 12/566,163 filed Sep. 24, 2009; and Ser. No. 12/566,193 filed Sep. 24, 2009; all of which claim the benefit of priority of Provisional Patent Application No. 61/239,506 filed Sep. 3, 2009 and all of which are a continuation-in-part of U.S. patent application Ser. No. 12/508,701 filed Jul. 24, 2009, which in turn claims the benefit of priority of Provisional Patent Application No. 61/222,206 filed Jul. 1, 2009, the entire disclosures of which are hereby incorporated by reference.

BACKGROUND OF THE INVENTION

The present invention relates to the field of obesity and diabetes and more specifically to minimally invasive systems and methods for controlling or treating obesity and/or type 2 diabetes.

Obesity is one of the leading preventable causes of death worldwide and has become a global epidemic affecting more than 400 million people. In the United States alone, approximately 300,000 obesity-linked deaths occur annually, and obesity-related co-morbities lead to nearly $150 billion in healthcare spending. Obesity is a medical condition associated with many subsequent diseases, including type-II diabetes, cardiovascular disease, sleep apnea and certain types of cancer. These conditions often have severe adverse effects on overall health, reduce quality of life, limit productivity, lead to significant medical costs, and can ultimately lead to reduced life expectancy.

While obesity has a range of contributing causes, the vast majority of obese individuals are obese because they overeat, fail to exercise adequately, and in some cases have genetic predispositions to weight gain. The primary treatment for obesity is dieting, routine physical exercise, and in some cases pharmacologic therapy. Obesity surgery, including irreversible Roux-en-Y gastric bypass (RYGB) and Laparoscopic Adjustable Gastric Banding (LAGB), involves surgical restriction of the stomach. These interventions are typically directed at either (i) reducing the caloric intake of the patient by triggering the satiety impulse more rapidly or physically removing the ability of the individual to ingest more than a limited amount of food, or (ii) inhibiting the ability of the individual's digestive system to extract the full caloric value of the food being eaten.

The current surgical treatments for obesity, although often effective in achieving sustainable weight loss and thus reducing associated co-morbidities, involve gross anatomical reconstruction of the digestive system, which may be irreversible. Unfortunately, as has become widely publicized in the print and broadcast media, there can be significant adverse events, complications, and/or mortality associated with the most radical of these procedures (including but not limited to RYGB). In a large number of patients, subsequent surgical procedure(s) are required to address the complication(s) from the original surgery. While use of RYGB and LAGB are approved for individuals with lower BMIs (i.e., <40), the risks associated with the procedures have limited their adoption and/or use to only the morbidly obese population (>40 BMI). Recent reports indicate that there is a need to expand the options for obesity surgery in order to provide safer alternatives for individuals who are not prepared to risk the adverse consequences of radical RYGB and LAGB surgery, but for whom a surgical intervention is wholly appropriate. In fact, many individuals who could benefit from surgical intervention before their excess weight results in serious health problems forego surgery due to the significant complications and high rates of long-term adverse events leading to poor quality of life. Thus, there is a growing need for an effective and safe alternative to obesity surgery for the obese patient population worldwide.

Diabetes mellitus type 2 or type 2 diabetes is a disorder that is characterized by high blood glucose in the context of insulin resistance and relative insulin deficiency. There are an estimated 23.6 million people in the U.S. (7.8% of the population) with diabetes with 17.9 million being diagnosed, 90% of whom are type 2. With prevalence rates doubling between 1990 and 2005, CDC has characterized the increase as an epidemic. Traditionally considered a disease of adults, type 2 diabetes is increasingly diagnosed in children in parallel to rising obesity rates due to alterations in dietary patterns as well as in life styles during childhood.

Type 2 diabetes is a chronic, progressive disease that has no established cure, but does have well-established treatments which can delay or mitigate the inevitable consequences of the condition. Often, the disease is viewed as progressive since poor management of blood sugar leads to a myriad of steadily worsening complications. However, if blood sugar is properly maintained, then the disease is effectively cured—that is, patients are at no heightened risk for neuropathy, blindness, or any other high blood sugar complication. Type 2 is initially treated by adjustments in diet and exercise, and by weight loss, most especially in obese patients. The amount of weight loss which improves the clinical picture is sometimes modest (2-5 kg or 4.4-11 lb); this is almost certainly due to currently poorly understood aspects of fat tissue activity, for instance chemical signaling (especially in visceral fat tissue in and around abdominal organs).

Gastric bypass procedures typically entail surgical restriction of the size of the stomach and rerouting or bypassing a proximal portion the intestine to reduce absorption of nutrients. A study of 20-years of gastric bypass patients found that 80% of those with type 2 diabetes before surgery no longer required insulin or oral agents to maintain normal glucose levels. Weight loss also occurred rapidly in many people in the study who had had the surgery. Unfortunately, gastric bypass procedures involve irreversible reconstruction of gastrointestinal anatomy and may be associated with significant adverse events, and/or mortality. In spite of the growth in the number of surgical procedures for weight loss (greater than 250,000 annually in the US), only 1.2% of eligible patients elect to undergo these invasive surgeries each year.

Many patients who could benefit from these procedures forego surgery due to the significant complications and high rates of long-term adverse events leading to poor quality of life. The estimated 0.3-2% mortality rate along with the 19% surgical complication rate for RYGB have been major barriers for expanding the use of surgery in broader patient populations.

In view of the foregoing, there is a need in the art for new devices and methods for controlling and treating obesity and type 2 diabetes.

SUMMARY OF THE INVENTION

The present invention provides systems, apparatus and methods for treating obesity and/or type 2 diabetes. In one aspect of the invention, an internal bypass device comprises a substantially hollow sleeve designed to extend from a proximal portion of the duodenum through at least a portion of the patient's small intestines. The sleeve is positioned such that partially digested food, i.e. chyme, moving through the digestive tract passes through the interior of the sleeve. This inhibits the absorption of nutrients/calories in the upper segments of the small intestine and delays mixing of chyme with digestive enzymes such that a quantity of food ingested by the patient will have a smaller caloric value with the sleeve in place.

In addition, several recent clinical studies have demonstrated that gastric bypass surgical procedures for treating obesity, including Roux-en-Y, bilio-pancreatic diversion and duodenum exclusion, show a rapid and remarkable reduction in clinical symptoms of diabetes including normalization of glucose and insulin levels. These effects occur before any changes in obesity and suggest that the duodenum may secrete molecular signals that cause insulin resistance. Supportive data has also been demonstrated in rat models of diabetes. See, Rubino and Marescaux, Annals of Surgery, 239 No. 1, 1-11 (January 2004), the entirety of which is incorporated herein by reference. Thus, the sleeve is designed to mimic the effects of bypassing the proximal portion of the small intestine seen in these surgical procedures. Specifically, it is believed that the sleeve will reduce hormonal triggers that may help to down-regulate the production of glucose, thereby resulting in a nearly immediate relief of Type-II diabetes symptoms. The stabilization or elimination of Type-II diabetes symptoms will have a beneficial impact on patient health and further increase weight loss.

In one aspect of the invention, the bypass device comprises a duodenal anchor configured for residing in a proximal portion of a duodenum of the patient and a flexible tube member coupled to the duodenal anchor and configured for extending through at least a portion of the duodenum of the patient. The anchor comprises an internal tube or support structure with an outer wall and an expandable element coupled to the outer wall of the tube and expandable to a size that exceeds the maximally dilated size of a human pylorus. The support tube and the expandable element preferably have a substantially cylindrical shape with a length in the longitudinal direction that is longer than their width in the radial direction. The expandable element tapers inward in the distal direction such that is proximal end has a larger diameter than its distal end when the expandable element has been expanded.

The size and shape of duodenal anchor has a number of advantages. The substantially cylindrical shape of the support tube and inflatable membrane inhibits turning of the device within the duodenal bulb of the patient. In particular, the longitudinal size of support tube is preferably longer than its diameter, thereby making it more difficult for the duodenum to turn the anchor on its side. This inhibits the duodenal anchor from becoming a blockage to the passage of chyme and fluids from the stomach through the small intestines. In addition, this configuration makes it more difficult for the anchor to be forced through the pylorus into the stomach by the forces exerted within the duodenum. In addition, the taper in the expandable element substantially conforms to the anatomy of the duodenal bulb of a patient. Thus, the anchor will cause less trauma to the tissue within the duodenal bulb.

In one embodiment, the expandable element is an inflatable balloon having a hollow interior and a valve for receiving a fluid to expand the balloon once it is in position within the proximal duodenum of the patient. In an exemplary embodiment, the duodenal anchor further comprises a rib element surrounding a portion of the internal support tube and housed within an interior of the expandable element. The rib element provides additional rigidity to the internal tube and ensures that the anchor retains its shape during expansion.

In an alternative embodiment, the bypass device comprises a duodenal anchor sized and shaped for residing in a proximal portion of a duodenum and a flexible tube member or hollow sleeve coupled to the duodenal anchor and configured for extending through at least a portion of the duodenum distal to the duodenal anchor. In this embodiment, the duodenal anchor is configured to exert a radially-directed force against the inner walls of the proximal duodenum. Preferably, this force is sufficient to expand the inner walls of the duodenum such that the anchor remains in position. This inhibits proximal and distal migration of the duodenal anchor and ensures that the hollow sleeve remains in place.

In an exemplary embodiment, the duodenal anchor comprises an internal support member having open proximal and distal ends and a biasing member coupled to the support member and exerting an outwardly directed force against the support member. The biasing member may comprise a spring or an annular rib that provides an external biasing force against the support member. Alternatively, the support member may comprise a shape memory material that naturally expands to a larger configuration upon positioning with the patient. The proximal end of the support member preferably has a larger diameter than the distal end of the support member such that the support member has a substantially funnel shape. This allows chyme passing through the pylorus to enter the proximal open end of the support member and pass through the hollow sleeve without contacting the inner walls of the duodenum outside of the sleeve.

In certain embodiments, the flexible tube or sleeve is coupled to a pair of anchors that reside on either side of the pylorus. The pair of anchors includes a gastric anchor positioned in the pyloric antrum of the stomach coupled to a duodenal anchor positioned in the proximal duodenum. The duodenal anchor is preferably configured according to one of the embodiments described above. The gastric anchor is movable between a collapsed configuration sized and shaped for advancement through an esophagus into pyloric antrum and an expanded configuration sized and shaped for inhibiting distal movement of the gastric anchor through the pyloric sphincter. The duodenal anchor is coupled to the hollow sleeve and movable between a collapsed configuration sized and shaped for advancement through the esophagus, the stomach and the pyloric sphincter into the proximal duodenum and an expanded configuration sized and shaped to inhibit proximal movement of the duodenal anchor through the pyloric sphincter.

A key advantage of the present invention is that the bypass device can be placed and removed endoscopically through the patient's esophagus in a minimally invasive outpatient procedure. In addition, the anchors expand to fit securely against tissue within the GI tract such that the position of the device is substantially maintained throughout the digestive process. Thus, the device is "self-anchoring" and does not require invasive tissue fixation within the patient's GI tract, thereby reducing collateral tissue damage and minimizing its impact on the digestive process. Also, unlike other more invasive procedures such as gastric bypass, the bypass device of the present invention does not require any permanent restructuring of the GI anatomy. Once the device is removed, the patient's GI tract should begin to function normally and in the same manner as if the device were never placed in the patient.

The gastric and duodenal anchors are preferably coupled to each other by one or more flexible columns that extend through the pyloric sphincter. The flexible columns allow both anchors to move back and forth within the stomach and duodenum, respectively, with the natural peristalsis motion of the patient. In the preferred embodiments, the gastric and duodenal anchors will periodically or continuously apply slight contact pressure to the distal portion of the pyloric antrum and the proximal portion of the duodenum, respectively. In an exemplary embodiment, the flexible columns comprise a flexible material that has sufficient tensile strength to withstand the strong peristalsis forces of the patient, such as silicone or the like.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 8 is a perspective view of a dissolvable proximal capsule of a delivery system according to the present invention;

FIG. 9 is a perspective view of a dissolvable distal capsule of the delivery system according to the present invention;

FIG. 10A is a partial cross-sectional view of the bypass device and the delivery system according to the present invention;

FIG. 19 illustrates another alternative embodiment of the present invention;

DETAILED DESCRIPTION OF THE PREFERRED EMBODIMENTS

Figure 1:
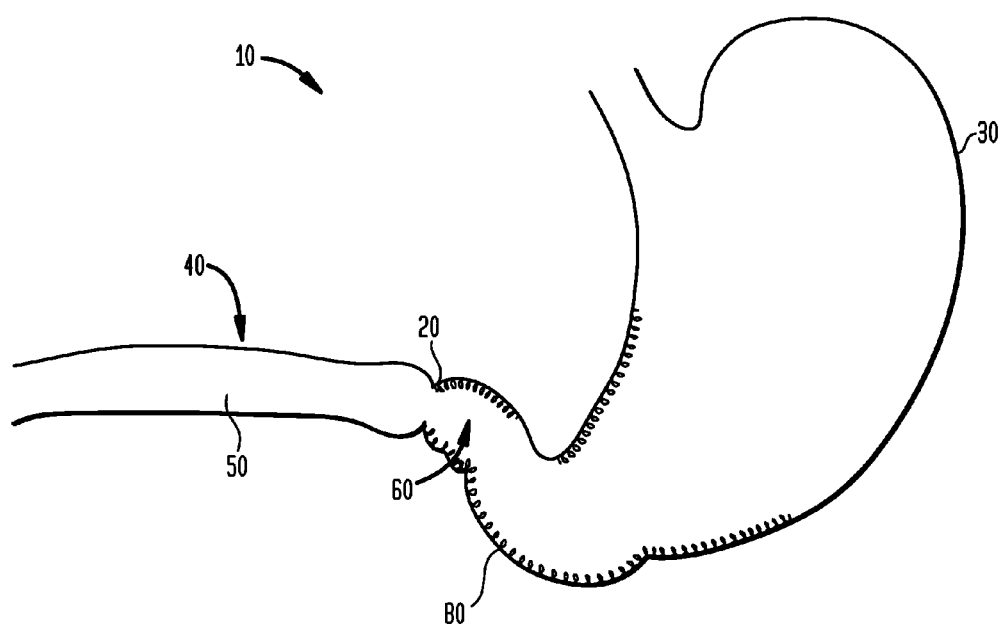
FIG. 1 is a view of a portion of a normal GI tract of a human.

In the present invention, systems, devices and methods are disclosed for treating and controlling obesity and/or type II diabetes. In particular, the systems and methods of the present invention provide an internal bypass of a proximal portion of the small intestines to inhibit contact between chyme and the bypassed small intestinal walls while allowing natural peristalsis to occur.

Diabetic foot ulcers are one of the major complications of diabetes mellitus. Foot ulcers occur in 15% of all patients with diabetes and precede 84% of all lower leg amputations. The significant increase in mortality among diabetic patients with foot ulcers observed over the past 20 years is considered to be due to the development of macro and micro vascular complications, including failure of the wound healing process.

Wound healing is a 'make-up' phenomenon for the portion of tissue that gets destroyed in any open or closed injury to the skin. Being a natural phenomenon, wound healing is usually taken care of by the body's innate mechanism of action that works reliably most of the time. The key feature of wound healing is the stepwise repair of lost extracellular matrix (ECM) that forms the largest component of the dermal skin layer. Therefore, controlled and accurate rebuilding becomes essential to avoid under or over healing that may lead to various abnormalities. But in some cases, certain disorders or physiological insults disturb the wound healing process that otherwise proceed smoothly in an orderly manner. Diabetes mellitus is one such metabolic disorder that impedes the normal steps of wound healing process. Many histopathological studies show a prolonged inflammatory phase in diabetic wounds, which causes a delay in the formation of mature granulation tissue and a parallel reduction in wound tensile strength.

High blood sugar levels prevent white blood cells, which are important in defending the body against bacteria and also in cleaning up dead tissue and cells, from functioning normally. When these cells do not function properly, wounds take much longer to heal and become infected more frequently. Also, long-standing diabetes is associated with thickening of blood vessels, which prevents good circulation including the delivery of enough oxygen and other nutrients to body tissues.

Another consequence of high blood sugar levels is that the body has difficulty producing many important components in the healing process, such as vascular endothelial growth factors (VEGF) and nitric oxide. For example, nitric oxide is known as an important stimulator of cell proliferation, maturation and differentiation. Thus, nitric oxide increases fibroblast proliferation and thereby collagen production in wound healing. Also, L-arginine and nitric oxide are required for proper cross linking of collagen fibers, via proline, to minimize scarring and maximize the tensile strength of healed tissue. Endothelial cell specific nitric oxide synthase (EcNOS) is activated by the pulsatile flow of blood through vessels. Nitric oxide produced by EcNOS, maintains the diameter of blood vessels and proper blood flow to tissues. In addition to this, nitric oxide also regulates angiogenesis, which plays a major role in wound healing.

Diabetic patients exhibit reduced ability to generate nitric oxide from L-arginine. Reasons that have been postulated in the literature include accumulation of nitric oxide synthase inhibitor due to high glucose associated kidney dysfunction and reduced production of nitric oxide synthase due to ketoacidosis observed in diabetic patients and pH dependent nature of nitric oxide synthase.

The present invention provides systems, apparatus and methods for treating wounds in patients, particularly chronic lower limb wounds in patients lacking the innate ability to regulate glucose (e.g., diabetic patients). In one aspect of the invention, a method for treating wounds includes positioning a flexible sleeve within the patient such that the sleeve extends through at least a portion of the duodenum to inhibit contact between chyme passing therethrough and at least a portion of an inner surface of the duodenum. The hollow sleeve is maintained within the duodenum for a sufficient period of time to reduce a blood glucose level in the patient. Preferably, the sleeve will be maintained in position for a sufficient period of time to permit the normalization of blood glucose levels in the patient (i.e., reducing such glucose levels to below about 150 mg, preferably below about 125 mg).

The sleeve creates an "internal bypass" that substantially inhibits contact between chyme and other substances entering the duodenum from the stomach of the patient and the bypassed portion of the duodenum. This reduces hormonal triggers that help to down-regulate the production of glucose, thereby resulting in the relief of certain symptoms that inhibit the body from effectively healing the wound, such as decreased peripheral vascular perfusion, neuropathy, a compromised or "inactive" immune system and a reduction in important components of healing, such as nitric oxide, vascular endothelial growth factors and the like.

In certain embodiments, the sleeve will be maintained in position for a sufficient period of time to increase the peripheral vascular perfusion in the patient. Patients lacking the innate ability to regulate glucose levels often suffer from decreased arterial perfusion of the extremities. The lack of blood flow to the extremities inhibits healing of wounds, such as foot ulcers and the like. In one embodiment of the present invention, the flexible sleeve is held in position within the duodenum until this process begins to reverse, thereby increasing peripheral vascular perfusion and allowing for accelerated healing of the wound.

In other embodiments, the sleeve will be maintained in position for a sufficient period of time to elevate an immune system response in the patient. Abnormally high glucose levels cause the body's immune system to become compromised or less active than normal. The white blood cells or leukocytes of the immune system that defend the body against infection become sluggish and unable to effectively fight infections, such as those associated with wounds. In this embodiment, the flexible sleeve is held in position within the duodenum until the activity of circulating leukocytes begins to substantially increase, which allows the patient's immune system to do its natural job of fighting the infection and accelerate healing of the wound.

In other embodiments, the flexible sleeve is maintained in position for a sufficient period of time to increase certain healing factors, such as nitric oxide and vascular endothelial growth factors (VEGF) in the patient. VEGF is an important signaling protein that stimulates the growth of new blood vessels, which can be a critical part of the angiogenesis process in wound healing. In one embodiment of the present invention, the flexible sleeve is held in position within the duodenum until a sufficient amount of VEGF are produced in the patient to accelerate healing of the wound.

In other embodiments, the flexible sleeve will be maintained in position for a sufficient period of time to halt or reverse neuropathy. Diabetic neuropathy is a common complication of patients lacking the innate ability to regulate glucose in which nerves are temporarily or permanently damaged as a result of high blood sugar levels (hyperglycemia). Neuropathy can complicate the wound healing process, particularly in the extremities. In this embodiment, the sleeve is held in position until nerves that have not been permanently damaged or destroyed can be repaired by the body to accelerate healing of the wound.

In a preferred embodiment, the flexible sleeve is sized and shaped to extend from the distal opening of the duodenal anchor through at least a portion of the duodenum (i.e., between about 2-12 inches). In some embodiments, the sleeve may extend throughout the duodenum and into a proximal portion of the jejunum of the patient (i.e., between about 12-30 inches, preferably about 12-16 inches). The sleeve is substantially hollow and positioned such that partially digested food, i.e. chyme, moving through the digestive tract passes through the interior of the sleeve. This inhibits the absorption of nutrients/calories in the upper segments of the small intestine and delays mixing of chyme with digestive enzymes such that a quantity of food ingested by the patient will have a smaller caloric value with the sleeve in place. In addition, it is believed that the sleeve inhibits certain hormonal triggers that would otherwise occur when food passes through the duodenum and proximal jejunum; hormonal triggers that cause the body to become insulin resistant and result in type 2 diabetes.

Applicant has discovered that there are sensory cells lining the small intestine, between the pylorus and the sphincter of Oddi (or ampula of vader) where the common bile duct empties bile and pancreatic juices into the duodenum that participate in the cascade of signaling hormones that control glucose management. These hormones include ghrelin, glucagon, insulin, and a few other ones that interact with the pancreas, brain, cell receptors, etc. In some cases, particularly in obese individuals, the control exerted by these sensory cells becomes dysfunctional, resulting in poor control of glucose in the body. By avoiding food/chyme contact with these sensory cells, the control over glucose levels in the bloodstream reverts to other mechanisms in the body that are not dysfunctional. These other control mechanisms allow the patient to maintain better control of glucose, thereby partially or completely resolving the symptoms of type II diabetes in these patients.

In certain embodiments, the sleeve is removably introduced through a natural orifice in the patient into the small intestines, preferably endoscopically through the patient's esophagus, stomach and pylorus. The sleeve can be maintained in position within the duodenum in a variety of ways known to those of skill in the art (e.g., sutures, hooks, barbs, atraumatic anchoring mechanisms and the like), typically for about 2 weeks to one year, although it may remain in place for longer periods of time.

In a preferred embodiment, the sleeve is maintained in position with a pair of anchor elements flexibly coupled to each other and the sleeve. In the preferred embodiment, the flexible anchors are endoscopically introduced with the sleeve and positioned on either side of the pylorus. The duodenal anchor element is preferably expanded to a size that will inhibit proximal movement of the duodenal anchor through the pyloric sphincter to ensure that the sleeve remains in the patient's intestines. Likewise, the gastric anchor element is expanded to a size that will inhibit or prevent distal movement through the pyloric sphincter to ensure that the device does not pass further into the intestines and create a blockage. In a preferred embodiment, the anchor elements are expanded by delivering a fluid into each anchor element to inflate said anchors. In other embodiments, the anchor elements may be expanded mechanically or by other suitable means.

Referring to the drawings, wherein like reference numerals refer to like elements, there is shown in FIG. 1 an example of a portion of a GI tract 10 of a human body. Two smooth muscle valves, or sphincters, contain the contents of the stomach within the stomach upon ingestion. They are the esophageal sphincter (not shown), found in the cardiac region above the antrum cardiacum, and the pyloric sphincter 20, disposed between the stomach 30 and the small intestine 40. The pylorus 35 is the region of the stomach 30 that connects to the duodenum 50. The pylorus 35 is divided into two parts: the pyloric antrum 60 which connects the body to the stomach and the pyloric canal which connects to the duodenum 50. The pyloric sphincter 20 is a strong ring of smooth muscle at the end of the pyloric canal that functions to help regulate the passage of chyme from stomach 30 to the duodenum 50.

Satiety receptors 80 are generally located all along the inside lining of stomach tissue. Partially undigested food in GI tract 10 is generally referred to as chyme. If chyme remains in the region of the stomach before flowing into small intestine 40, satiety receptors 80 have a greater chance of being activated, which enhances the ability of an overweight or obese patient to feel satiated and suppresses the desire to eat.

Pyloric antrum 60 and duodenum 50 are innervated by the enteric nervous system and the parasympathetic nervous system (i.e., the vagus nerve). Many researchers have shown that the vagus nerve is responsible for the majority of afferent signals responsible for satiety. Thus, it is believed that increasing the afferent vagal nerve activity will result in satiety signals produced by the brain, making the patient feel more full and less inclined to eat.

A bypass device according to any of the below-described embodiments is preferably comprised of a polymeric structure that is compliant and generally flexible and bendable. Preferably, at least a portion of the device is made of silicone although other materials may be used such as polyurethane, polyethylene, GORE-TEX®, Teflon® and the like. Some portions of the device may be thicker than others for enhanced strength properties and to enhance the capability of the device to resist the natural peristaltic action of GI tract 10. Alternatively, some portions of the device may be thinner than others to allow for the material peristaltic actions of GI tract 10 to occur without the device providing a counteractive force. Preferably, if a portion of the device is bent or twisted during insertion, its polymeric structure will allow it to revert back to its resting or initial shape.

The one or more materials that comprise a bypass device according to the present invention are preferably selected for their ability to yield and flex during implantation and removal of the device. These properties also protect the patient and the tissues and organs with which the device comes into contact. The compliant nature of the bypass device allows its configuration to be manipulated during a surgical procedure, preferably in such a way that the device tends to revert to its operative configuration. The device may be made of shape memory material, such as nitinol or other known pliable polymeric materials, to allow for expansion back into its operative configuration. Any or all of the device may be coated with a suitable material such as Teflon or Parylene to provide a smooth outer surface to reduce friction between the device and the patient during implantation and removal.

The bypass device according to the present invention is structured to inhibit the rate that chyme passes through GI tract 10, thereby enhancing the ability of chyme to activate satiety receptors 80 and effectively enhance satiety in a patient. In particular, the device is preferably structured to reduce the rate of gastric emptying such that obesity can be controlled by controlling satiety.

The bypass device of the present invention is also designed to provide periodic or continuous contact pressure on the pyloric antrum and or the proximal portion of the duodenum. This contact pressure modulates (preferably stimulates) one or more nerves within these two structures, thereby increasing their activity. In certain embodiments, this contact pressure is brought about by the design of the device; namely, the flow restrictor and anchor are coupled to each other by flexible elements or columns (discussed in detail below). These flexible columns are sized such that the anchor generally rests against the proximal portion of the duodenum and the flow restrictor generally rests against the distal portion of the pyloric antrum. The flexible columns also have enough "give" or flexibility to allow the anchor and flow restrictor to move back and forth with the peristaltic motion of the GI tract. Thus, the anchor and flow restrictor may periodically move away from the proximal portion of the duodenum and the distal portion of the pyloric antrum, respectively. However, they will generally move back in contact with these structures to provide at least periodic pressure contact on these structures to stimulate the vagus nerves therein.

The bypass device is also designed to inhibit contact between chyme passing through the duodenum and the inner walls of the duodenum. This inhibits the absorption of nutrients/calories in the upper segments of the small intestine and delays mixing of chyme with digestive enzymes such that a quantity of food ingested by the patient will have a smaller caloric value with the sleeve in place. In addition, this reduces hormonal triggers that may help to down-regulate the production of glucose, thereby resulting in a nearly immediate relief of Type-II diabetes symptoms. The stabilization or elimination of Type-II diabetes symptoms will have a beneficial impact on patient health and further increase weight loss.

Incretins are gastrointestinal hormones, produced in response to the transit of nutrients that boost insulin production. Because an excess of insulin can determine hypoglycemia (extremely low levels of blood sugar)—a life-threatening condition, it has been speculated that the body has a counter-regulatory mechanism (or "anti-incretin" mechanism), activated by the same passage of nutrients through the upper intestine. The latter mechanism would act to decrease both the secretion and the action of insulin. Thus, in healthy patients, a correct balance between incretin and anti-incretin factors maintains normal excursions of sugar levels in the bloodstream. In some individuals, however, the duodenum and jejunum may be producing too much of this anti-incretin, thereby reducing insulin secretion and blocking the action of insulin, ultimately resulting in Type 2 diabetes.

Indeed, in Type 2 diabetes, cells are resistant to the action of insulin ("insulin resistance"), while the pancreas is unable to produce enough insulin to overcome the resistance. After gastrointestinal bypass procedures, the exclusion of the upper small intestine from the transit of nutrients may offset the abnormal production of anti-incretin, thereby resulting in remission of diabetes. However, it should be noted that the scientific community has not settled on a particular mechanism of action that causes patients undergoing such bypass procedures to more less "insulin resistant". Thus, the present invention is not limited to this particular mechanism of action or any particular mechanism of action.

Certain components of the bypass device according to the present invention may be discussed as being attached or connected to one another. Preferably, the device is constructed of one continuous piece and of one material, preferably silicone. However, two or more components of the device may be manufactured separately and subsequently assembled. If assembled, components may be glued together using a silicone-based glue.

Figure 2:
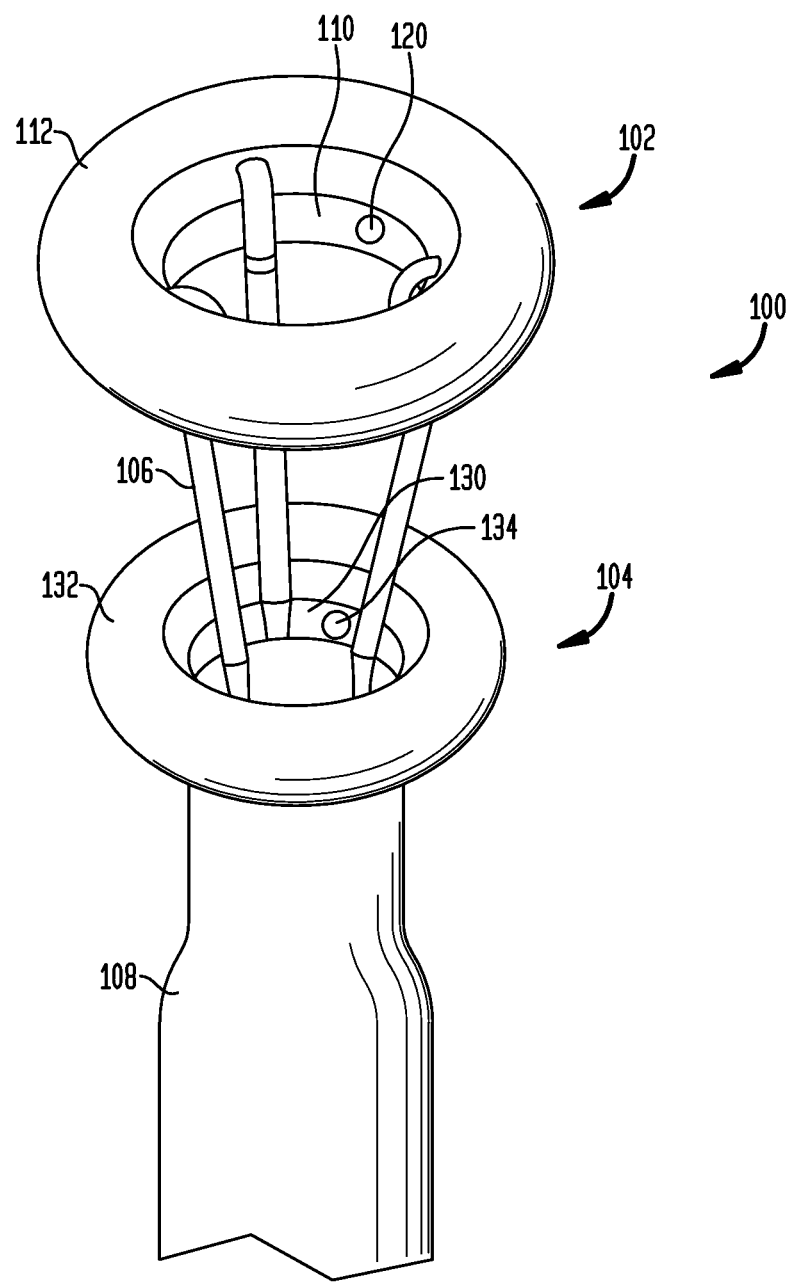
FIG. 2 is a perspective view of a bypass device in an operative configuration according to one embodiment of the present invention.

FIG. 2 illustrates one preferred embodiment of a bypass device 100 according to the present invention. As shown, device 100 includes a gastric anchor 102 coupled to a duodenal anchor 104 by a plurality of flexible silicone tethers or pyloric columns 106 and a hollow sleeve 108 coupled to the distal end of duodenal anchor 104. Pyloric columns 106 are designed to extend through the pyloric sphincter 20 to allow both gastric anchor 102 and duodenal anchor 104 to have some limited movement back and forth within the stomach 30 and duodenum 50, respectively, with the natural peristalsis motion of the GI tract (see FIG. 16). Pyloric columns 106 may be cylindrical or any other type of prismic shape and are preferably designed such that the distance between the distal end of gastric anchor 102 and the proximal end of duodenal anchor 104 is about 10-60 mm, preferably about 20-40 mm, and more preferably about 30 mm, in the fully extended, but relaxed condition (i.e., non-elastically extended). Preferably, device 100 includes at least two, preferably three, pyloric columns 106 each having a diameter of about 1-5 mm which are attached to the inside surfaces of anchors 102, 104. Alternatively, anchors 102, 104 may be coupled together with a hollow sleeve that extends through the pyloric sphincter 20. The sleeve would preferably be sufficiently flexible to allow sphincter 20 to open and substantially close without hindrance from the sleeve.

In an alternative embodiment, device 100 may include a single pyloric column 106 that extends between the gastric and duodenal anchors. Optionally, the single column may form multiple (i.e., 2-4) column segments on its distal and proximal ends for coupling to the duodenal and gastric anchors, respectively. Preferably, the column segments will be short enough such that the gastric column segments substantially remain in the stomach (i.e., do not pass through the pylorus) and the duodenal column segments substantially remain in the duodenum. In this manner, a single column will pass through the patient's pylorus, thereby causing less trauma and/or intrusiveness on the pylorus. The multiple column segments provide more support to the gastric and duodenal anchor fixations points. In addition, separating the column segments from each other so that each of the column segments are coupled to a single column therebetween minimizes twisting of the columns relative to each other. For example, if the gastric anchor is rotated by the stomach antrum while the duodenal anchor is held in place within the duodenal bulb, the column segments coupled to the gastric anchor will twist relative to each other. However, this twisting will not translate to the single column or the column segments coupled to the duodenal anchor. This minimizes any potential blockage that could otherwise occur if the columns passing through the pylorus twisted around each other.

In yet another embodiment, the pyloric column(s) have a length sufficient to substantially separate the forces applied to each of the anchors from each other. Thus, the columns will have a length of at least 8 cm and preferably between about 8-15 cm, more preferably about 10-13 cm. Thus, forces exerted on the gastric anchor by the stomach antrum will cause the gastric anchor to be moved in a variety of different directions within the stomach. In particular, the stomach antrum will often squeeze down on the gastric anchor and pull it proximally towards the esophagus. The longer columns in this embodiment will allow the gastric anchor to move a considerable distance away from the pylorus without exerting a pull force on the duodenal anchor to thereby pull the duodenal anchor past the pylorus and into the patient's stomach.

Figure 3:
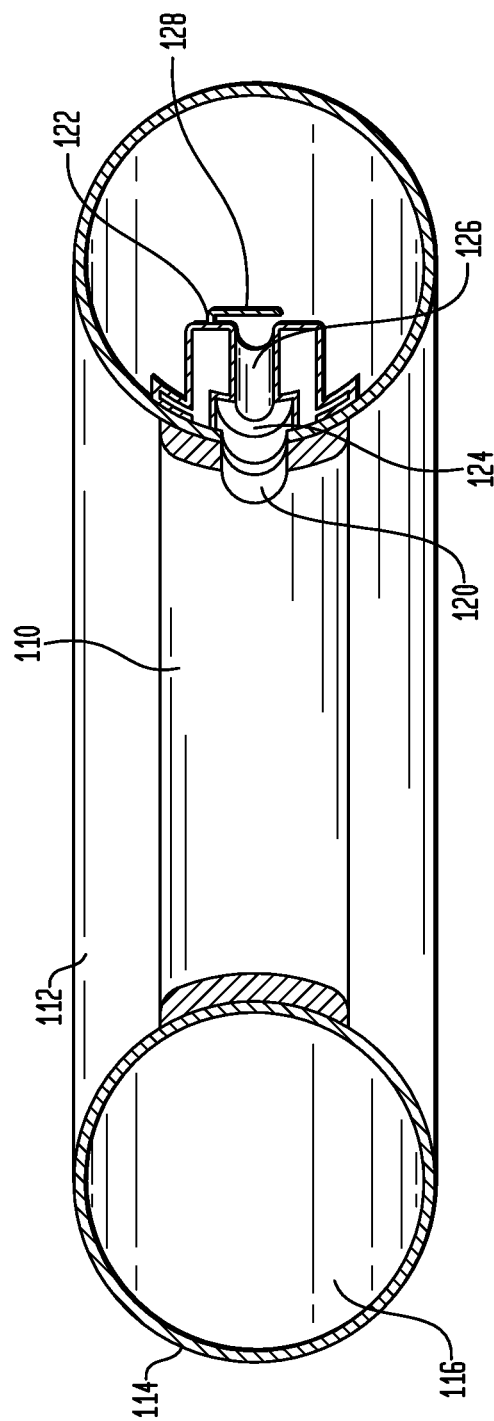
FIG. 3 is a cross-sectional view of a gastric anchor of the bypass device of FIG. 2.

FIG. 3 illustrates a cross-sectional perspective view of an exemplary embodiment of gastric anchor 102. As shown, gastric anchor 102 includes an internal ring 110 coupled to an annular inflatable membrane 112 having a substantially annular or toroidal shape. Inflatable membrane 112 comprises an outer wall 114 surrounding a hollow interior 116 configured for inflation via a suitable fluid. Ring 110 and membrane 112 preferably comprise a flexible biocompatible material, such as a phosphlipid resistant silicone material (e.g., a fluorosilicone copolymer). Alternatively, ring 110 may comprise a water-absorbent material, such as a hydrogel, that expands and hardens upon contact with fluid. Ring 110 provides structural support for anchor 102, while inflatable member 112 allows anchor 102 to move between a collapsed configuration for introduction through the patient's esophagus and an expanded configuration within the stomach. Thus, ring 110 is preferably harder and less flexible than inflatable membrane 112 having a durometer of at least about 70 A, preferably greater than about 80 A, while membrane 112 preferably has a durometer between about 30-60 A, more preferably between about 40-60 A.

In an alternative embodiment, anchor 102 may simply include an inflatable member 112 without support ring 112. In this embodiment, the inflatable member 112 would be inflated to a size and pressure sufficient to withstand peristalsis forces without compressing to a size that would allow the anchor 102 to pass through pyloric sphincter 20.

Gastric anchor 102 further includes a fluid inlet 120 for delivery of a fluid into hollow interior 116 of membrane 112. In the preferred embodiment, fluid inlet 120 comprises a valve 122 formed along the inner circumference of ring 110 and extending into interior 116 of membrane. As shown, valve 122 includes small chamber 124 in which a hole 126 is formed. Hole 126 extends radially from the inner surface of ring 110, through ring 110, into interior 116 of membrane 112. A flexible silicone flap 128, formed as part of the interior surface of the inflatable member 112, is located adjacent to hole 126. Silicone flap 128 serves to occlude hole 126 once the pressure within interior 116 of inflatable member 112 exceeds the pressure exterior to the member 112, thereby forming a one-way valve to prevent fluid egress from membrane 112.

In addition to, or as an alternative to, the one-way valve, a curable fluid, such as silicone, may be injected into the fluid pathway after the saline. The curable fluid will cure and harden, thereby preventing any fluid egress from the interior of inflatable member 112. In another embodiment, the inflatable members of the anchors may comprise a material that self-seals when punctured with a very sharp small instrument such as a syringe. In this embodiment, the inflatable members of the bypass device may simply be inflated with a syringe and then self-sealed by the material to prevent fluid egress. In yet another embodiment, the anchor may comprise a small ring that surrounds an opening for passage of a needle, such as a syringe. The ring is designed to close over the opening when the needle is withdrawn from the anchor to thereby close over the valve and prevent egress of fluid after the anchor has been inflated.

In the preferred embodiment, the valves of the gastric and duodenal anchors are coupled to fluid tubes that are long enough to pass through the patients esophagus and mouth. In this manner, fluid can be delivered from outside of the patient's body to the anchors after they have been positioned around the patient's pylorus (discussed in detail below). In certain embodiments, the fluid tubes may be detachable from the anchors such that they can easily be detached and pulled out of the patient's body after the inflation process. In other embodiments, the fluid tubes will be designed such that they can be cut by the physician (with a suitable endoscopic cutting device) inside of the patient's GI tract after the anchors have been inflated.

In the preferred embodiment, ring 110 has an inner diameter of about 10-50 mm, preferably about 20-40 mm, and more preferably about 30 mm, and a thickness of about 1-5 mm, preferably about 3 mm. Inflatable membrane 112 has an outer diameter of about 30-70 mm, preferably about 40-50, and more preferably about 45 mm, when the pressure within membrane 112 is equal to the pressure outside (the state of nominal inflation, i.e., complete inflation without elastic deformation). In the preferred embodiment, however, membrane 112 is designed such that fluid can be injected into interior 116 until it has expanded significantly beyond the initiation of elastic deformation, with a maximum exterior diameter of the implanted gastric portion preferably being between about 50 and 60 mm.

It should also be understood that gastric anchor 102 may have a variety of different shapes (other than toroidal) and a variety of different volumes that that described above. For example, gastric anchor 102 may comprise a substantially cylindrical shape to provide a height that is larger than its width. In this embodiment, the shape of the anchor will prevent it from rotating in the stomach antrum and passing through the pylorus. In addition, gastric anchor may have a larger volume to provide a stronger anchor in the patient's stomach antrum. A larger volume gastric anchor may also provide an increased satiety effect on the patient.

Duodenal anchor 104 preferably has a similar structure as gastric anchor 102; including an inner ring 130 and an annular inflatable membrane 132 having a substantially annular or toroidal shape (see FIG. 2). Inflatable membrane 132 is designed to inflate into a substantially annular shape that provides for a secure anchor against the distal opening of the pyloric sphincter. This ensures that anchor 104 will remain in place within the duodenum 50 despite the natural peristalsis forces acting against anchor 104. Anchor 104 further includes a valve structure 134 (similar in design to gastric anchor 102) for delivering a fluid into an interior of membrane 132 to inflate membrane 132. In the exemplary embodiment, ring 130 has an inner diameter of between about 10-20 mm, preferably about 15 mm, a thickness of between about 1-5 mm, preferably about 3 mm. Inflatable membrane 132 preferably has an outer diameter of between about 20-30 mm, preferably about 25 mm, when the pressure within membrane 132 is equal to the pressure outside (the state of nominal inflation, i.e., complete inflation without elastic deformation). Similar to the gastric component, membrane 132 is designed for inflation beyond the initiation of elastic deformation, with a maximum exterior diameter of the implanted duodenal anchor being between about 30 and 50 mm, preferably between about 35 to 40 mm.

In an alternative embodiment, gastric and duodenal anchors 102, 104 include one or more expandable components that either completely or partially replace the fluid used in the previous embodiment to inflate or expand anchors 102, 104. In a preferred embodiment, the expandable components comprise fluid-absorbent materials designed to expand upon contact with certain fluid, such as hydrogels. Hydrogels are networks of polymer chains that are water-insoluble and hydrophilic. In this embodiment, a plurality of hydrogel components (not shown) are housed within the inflatable members of anchors 102, 104. The hydrogel components will be introduced into the patient in the "dry" or smaller state within anchors 102, 104. A fluid, such as saline, is delivered into the interior of the inflatable members and is absorbed within the hydrogel components (which may be of any shape, such as spheres or the like) to expand these components, thereby expanding the inflatable members.

In one aspect of this embodiment, the anchors 102, 104 include a plurality of hydrogel beads, preferably about 0.5 to 3.0 mm in diameter, designed to expand to a larger size (e.g., about 4-6 mm in diameter) upon hydration with a fluid, such as saline. In this embodiment, anchors 102, 104 may or may not include inner rings 110 and they may not require one-way valves. The hydrogel balls provide additional rigidity to the anchors 102, 104. In addition, they provide additional safety in the event that the inflatable members are punctured with a small hole as the balls will remain within inflatable members in such event (as opposed to a puncture that will allow all of the fluid to exit inflatable members in the previous embodiments). Upon removal of the device, the inflatable members will be punctured with a large enough hole to allow the hydrogel balls to exit the interiors of the inflatable members. The hydrogel balls can be allowed to pass through the patient's GI tract and excreted naturally.

Figure 4:
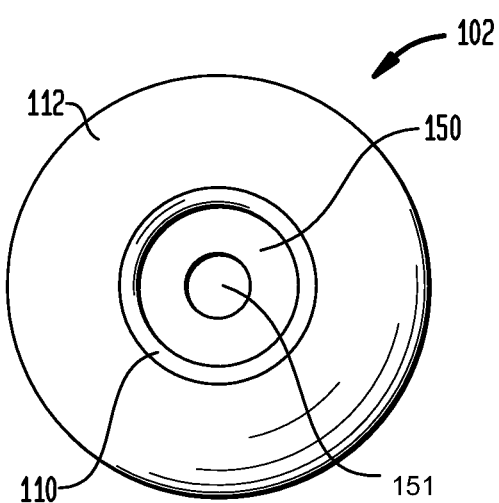
FIG. 4 is a top view of an alternative embodiment of a gastric anchor according to the present invention.

FIG. 4 illustrates an alternative embodiment of gastric anchor 102. In this embodiment, anchor 102 is substantially similar in design and construction as the anchor shown in FIG. 2, comprising a central support ring 110 surrounded by an inflatable member 112 having an internal valve 120. However, this anchor 102 also includes an internal restrictor plate 150 attached to support ring 110. Plate 150 has a central hole 151 designed to allow chyme to pass therethrough. Plate 150 serves to substantially inhibit the flow of chyme from the stomach to the pyloric sphincter. It is believed that this will cause the prolongation of satiety, and result in fewer meals being eaten and/or smaller meals being ingested. The inner diameter of hole 151 will vary depending on the rate of chyme flow desired for the individual patient. For example, hole 151 may have a diameter of about 5-20 mm.

Figure 5:
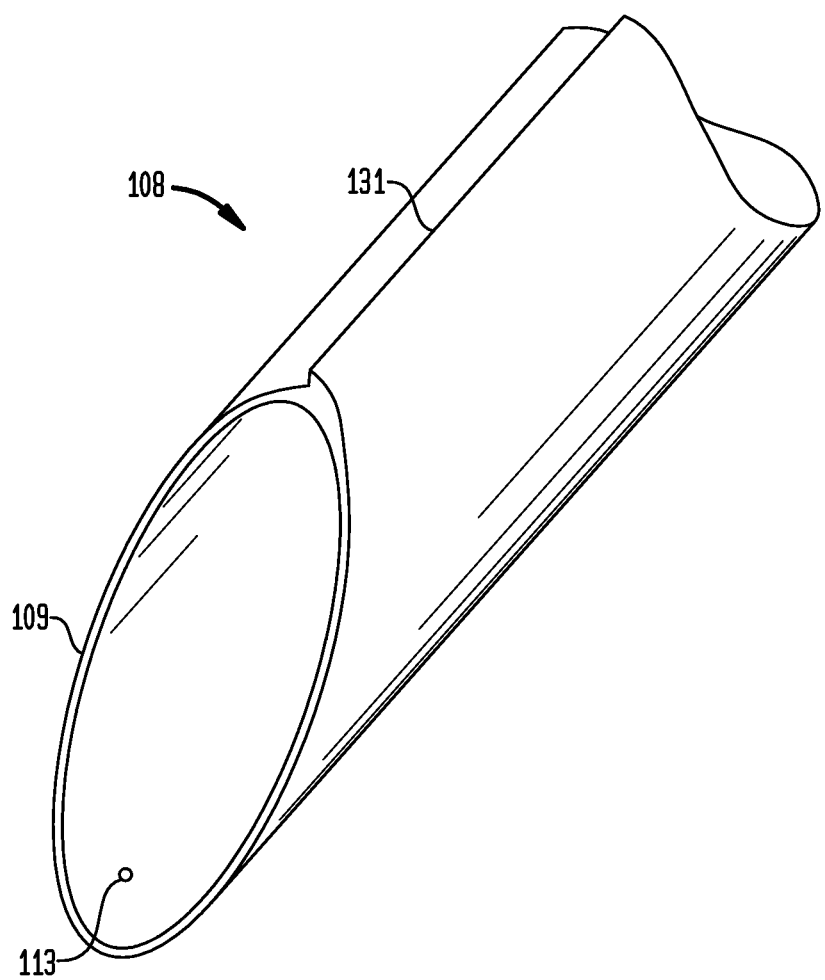
FIG. 5 illustrates a distal end of a hollow sleeve according to the present invention.

Referring to FIG. 5, sleeve 108 may be manufactured to any length according to a particular patient and/or surgical procedure, and in the preferred embodiment includes at its distal end a beveled tip 109. Along its length, sleeve 108 may have one or more side holes 113 which provide further access for chyme to enter sleeve 108. In some embodiments, a rib 131 is disposed along sleeve 108 and is preferably substantially parallel to the longitudinal axis of sleeve 108, though rib 131 may extend only partially along sleeve 108 and may take on a curved or other type of orientation with respect to the longitudinal axis. Rib 131 may be comprised of silicone and additionally may include a radiopaque material, such as barium, so that rib 131 may be detected by a fluoroscope. Rib 131 may be provided as a separate component and later attached to sleeve 108, or rib 131 may essentially be the overlapping seam formed during the manufacture of sleeve 108 when a flat piece of material is rolled into a tubular shape. In such a configuration, sleeve 108 may be comprised of a homogenous material attached by a radiopaque glue. Of course, as rib 131 is primarily used as an aid during implantation and/or removal of obesity device 100, rib 131 need not necessarily be included in this or any other embodiment according to the present invention.

Sleeve 108 preferably has a diameter that will substantially correspond with the inner diameter of the patient's duodenum and a length that will allow the sleeve to extend into at least the proximal portion of the jejunum depending on the individual patient's anatomy. Thus, sleeve 108 will typically have a length of between about 20-80 cm, preferably between about 55-75 cm, a thickness of about 0.05 mm to 0.22 mm and a diameter of between about 1 to 3 cm, preferably about 2.5 cm. Preferably, the proximal portion of sleeve 108 has an inner diameter of about 1.2 cm that expands laterally in the proximal direction to 1.5 cm so that it may be sealed to the lower surface of anchor 104. The material of the sleeve is preferably silicone, such as a polyethylene-reinforced silicone.

Sleeve 108 may include one or more markers (e.g., barium) designed for viewing the position of the sleeve within the intestines through fluoroscopy, such as rib 131 or other markers that are spaced along the length of sleeve 108. In addition, sleeve 108 may further include components that inhibit twisting or kinking of the sleeve 108. In one embodiment, these components include one or more stiffening elements, such as rings, coupled to either the inside or the outside of the sleeve at spaced locations along its length. These rings can, for example, be made of a slightly thicker silicone material that would resist twisting or kinking of the sleeve around the ring. In other embodiments, the stiffening elements may be in spiral shape or extending lengthwise along at least a portion of the sleeve 108.

Sleeve 108 may also include one or more internal lumens extending along a portion of or the entire length of the sleeve. The fluid lumens comprise a proximal end configured for coupled to a fluid delivery system to allow a fluid to flow through sleeve to extend sleeve through the patient's duodenum and/or to ensure that sleeve remains patent without any twists or kinks along its length. In one embodiment, the sleeve comprises multiple (e.g., 2-5) internal lumens extending from the proximal to the distal end of the sleeve and spaced from each other around the circumference of the sleeve. In another embodiment, the sleeve comprises an internal lumen that extends in a spiral pattern down the length of the sleeve.

In yet another alternative embodiment, sleeve 108 may further include one or more fluid chamber(s) coupled to one or more of the internal lumens. The fluid chamber(s) facilitate implantation of the sleeve within the patient by allowing the physician to at least partially fill one or more of the chambers before withdrawing the scope from the duodenum (discussed in more detail below). In addition, the fluid chambers provide stiffness to the sleeve to provide more stability to the sleeve and ensure that it remains in place within the patient after implantation. The fluid may also include a material that is observable under fluoroscopy (e.g., barium or the like) such that the location of the internal lumens and/or the fluid chambers can be viewed by a physician after implantation.

In one embodiment, the fluid chamber comprises an annular passage extending around the circumference of the sleeve at or near its distal end. This configuration provides the additional advantage that, when filled, the annular fluid chamber provides a distal anchor for the sleeve and the entire bypass device to provide additional against proximal migration of the sleeve and/or device. In another embodiment, the sleeve comprises multiple annular fluid chambers spaced along the length of the sleeve to provide additional rigidity to the sleeve, thereby ensuring that the sleeve remains patent and preventing any kinking or twisting along its length.

In an alternative implantation method, the sleeve 108 may be initially folded "accordion-style" and tucked into the interior of the anchor 104. The distal end of sleeve 108 is initially closed, with a small silicone rubber knob (not shown) attached to the bottom of sleeve 108 (e.g., like a "sock" with a ball on the inside surface of the "toe"). Just proximal to the ball, at a region where the diameter of sleeve 108 is about 2.1 cm, is a circumferential perforation (not shown) such that the ball and the "toe portion" of the sleeve will tear away from sleeve 108 leaving an open tubular sleeve behind.

Figure 6:
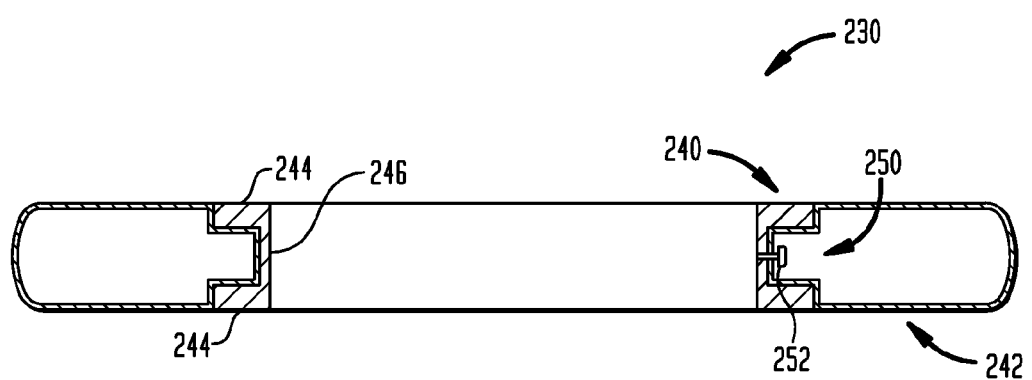
FIG. 6 is a cross-sectional view of an alternative embodiment of a duodenal anchor according to the present invention.
Figure 7:
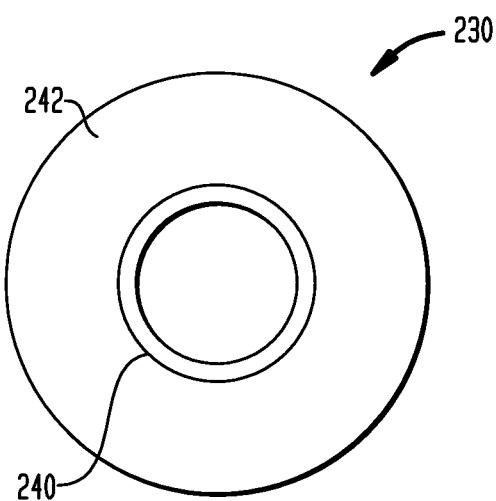
FIG. 7 is a top view of the duodenal anchor of FIG. 6.

Referring now to FIGS. 6 and 7, an alternative embodiment of a duodenal anchor 230 will now be described. As shown, anchor 230 comprises an annular support ring 240 coupled to an inflatable flexible membrane 242. In this embodiment, support ring 240 comprises two flat ring elements 244 connected together by a semi-rigid central ring 246 that holds the flat ring elements 244 apart from each other. Flat ring elements 244 and central ring 246 preferably comprise a suitable material, such as silicone, which may be molded as one-piece or molded separated and glued together with a suitable silicone glue. Flat ring elements 244 are preferably separated from one another by a distance of about 8-12 mm. Flexible membrane 242 is sealed to the exterior circumferential surfaces of flat ring elements 244 and central ring 246. Membrane 242 is initially tucked in a space 250 between flat ring elements 244 with sufficient additional material such that when saline is injected into the interior of membrane 242, an inflated "inner tube" structure is created. This inner tube structure is intended to inflate to a maximum diameter of between 30-45 mm (depending on the specific duodenal anatomy of a given patient).

A one-way valve 252 is disposed between ring elements 244 at one location around the circumference thereof and directed inwardly. This valve 252 is initially coupled to a thin tube (not shown) that extends up along the exterior of the gastric anchor through which membrane 242 can be inflated. In an exemplary embodiment, a small wire (not shown) is incorporated into the seal of the inner membrane 242 to the rings to permit simple and rapid deflation of membrane 242 for removal of the device. A small ball (not shown) may also be coupled to the wire and located external to ring elements 244 and membrane 242 for grasping by an endoscopic instrument. Pulling the ball causes the wire to tear through membrane 242 and the seal, thus rupturing membrane 242 and collapsing anchor 230.

Referring now to FIGS. 8-10B, bypass device 100 further comprises a deployment system 200 for facilitating the deployment of device 100. As shown in FIGS. 8 and 9, deployment system 200 includes a proximal housing or capsule 202 and a distal housing or capsule 204. Capsules 202, 204 both comprise a biocompatible dissolvable material, such as gelatin and the like, designed to dissolve within the patient's body. As shown in FIG. 8, distal capsule 204 is sized and shaped to house sleeve 108 in a folded, compressed or collapsed configuration and duodenal anchor 104 in its collapsed or deflated configuration (see FIG. 10A). Distal capsule 204 is open at its proximal end, and has a bullet-shaped distal tip 208 with a small hole 206. Distal tip 208 is designed to facilitate passage of the capsule 202 (and sleeve 108 and anchor 104 therein) through the pylorus and into the duodenum. Hole 206 is sized and shaped for passage of a guidewire therethrough (see FIGS. 11-15). Capsule 202 is preferably about 80-160 mm long (preferably about 100-140 mm long) about 10-30 mm wide (preferably about 20 mm) and is preferably constructed to survive for less than 30 minutes before dissolving in the human intestines.

As shown in FIG. 9, proximal capsule 202 is sized and shaped to house gastric anchor 102 in its collapsed configuration and at least a portion of columns 106 therein (see FIG. 10A). Proximal capsule 202 is substantially cylindrically shaped and is primarily designed to facilitate passage of these components through the esophagus to minimize any damage to the inner walls of the esophagus. To that end, capsule 204 has a slightly curved distal end 205 with an opening 207 that is larger than distal opening 206 of distal capsule 204 to accommodate the various components of bypass device 100 therethrough, such as flexible columns 106; delivery structure 150 and fluid tube 210 (see FIG. 108). In the preferred embodiment, capsule 202 is about 30-70 mm long (preferably about 50 mm) and about 10-30 mm wide (preferably about 20 mm). Capsule 202 preferably comprises a material that will dissolve in less than 15 minutes within the human stomach, such as gelatin and the like. Alternatively, capsules 202, 204 may comprise a resorbable material or a material that can be safely excreted by the patient.

Figure 10B:
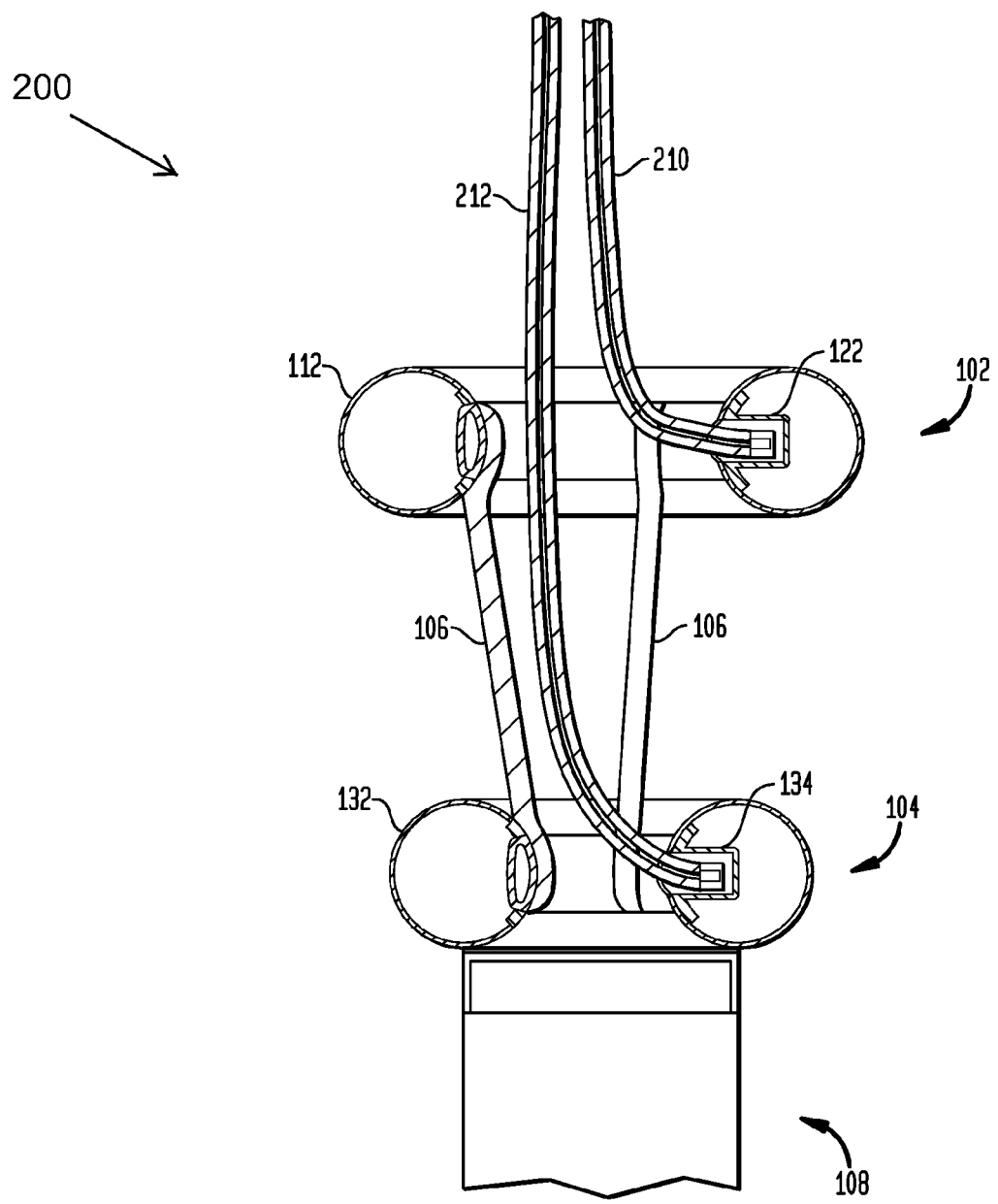
FIG. 10B is a cross-sectional view of a portion of the bypass device with fluid tubes of the delivery system still coupled thereto.

Referring now to FIGS. 10A and 10B, deployment system 200 further includes fluid tubes 210, 212 coupled to valves 122; 134 of gastric and duodenal anchors, respectively. Tubes 210, 212 each include small one-way valves (not shown), such as an umbrella valve or a duckbill valve, formed in their distal tips. Tubes 210, 212 are preferably coupled to valves 122, 134 such that their own own-way valves are formed within the small chambers 124 of valves 122, 134. Upon inflation of the respective components, the tubes 210, 212 are then cut proximal to valves 122, 134 such that their one-way valves provide additional protection to ensure that fluid injected into the inflatable membranes 112, 132 cannot escape through the holes.

Deployment system 200 further comprises a central tube structure 150 designed to extend through bypass device 100 (i.e., through the center of gastric and duodenal anchors 102, 104 and sleeve 108). Central tube structure 150 has a support tube 152 with an inner lumen (not shown) sized for passage of a guidewire therethrough (discussed in detail below). Support tube 152 has an inner diameter of at least 2.8 mm and preferably about 3 mm. Support tube 152 extends through hole 206 in distal capsule 204 and preferably has widened distal tip 155 designed to engage the outer surface of distal tip 208 of capsule 204. This facilitates passing of guidewire into the distal opening of support tube 152. Alternatively, support tube 152 may comprise an enlarged distal end (not shown) having a larger diameter than hole 206 that is located within capsule 204. In this embodiment, the enlarged distal end of support tube 152 operates to push against capsule to propel capsule 204 forward as it advances through the patient's GI tract. Support tube 152 preferably comprises a material that has sufficient flexibility to easily navigate the patient's small intestines, yet sufficient rigidity to allow for a pushing force from outside of the patient's body to advance tube 152 and the rest of bypass device 100 through the patient's GI tract (discussed below). Suitable materials for support tube 152 are polypropylene and the like.

Central tube structure 150 further comprises a flexible tube 154 extending alongside support tube 150. Flexible tube 154 houses a wire 156 coupled to a snare or a clamp 158 at its distal end. An actuator, such as a handle 160 (see FIG. 11), is coupled to the proximal end of wire 156 for opening and closing clamp 158. As discussed below, flexible tube 154 and clamp 158 are designed to facilitate advancement of sleeve 108 through the patient's small intestines to its final deployment position. Note that flexible tube 154 and support tube 152 may alternatively comprise a single tubular structure with two separate lumens (one for wire 156 and one to accommodate the guidewire).

In one embodiment, sleeve 108 comprises one or more small extensions or polyps (not shown) extending from its distal tip. In this embodiment, tube 154 includes a distal tip (not shown) with a clamp or fastener designed to fasten to the polyps to facilitate advancement of sleeve 108 as discussed above. When the sleeve is in its final deployment position, an actuator on handle on the proximal end of the tube 154 allows the use to pull the clamp proximally relative to the distal tip to sever the polyps and thereby detach tube 154 from the sleeve 108. At this point, central tube structure 150 can be removed from the patient. The polyps will then pass through the patient's GI tract in a normal manner.

In an alternative embodiment, deployment system 200 includes a thin, hollow sheath coupled to a silicone ball (not shown). The ball is detachably coupled to the distal end of sleeve 108 and the sheath extends through sleeve 108 and duodenal and gastric anchors 102, 104. The ball has an axial hole formed therethrough aligned with the axial bore of the sheath. The axial bore of the flexible sheath has a length of about 120 mm, and an outer diameter of about 5 mm. The sheath and ball together allow the user to advance sleeve 108 through the intestines to its final deployment position.

In reference to FIGS. 11-16, a method of implanting and removing a bypass device 100 according to the present invention will now be described. While the description of this method will be specifically directed to the embodiments illustrated in FIGS. 2 and 3, it will be understood by those skilled in the art that this method (or similar methods) can be used to implant and remove all of the embodiments of the present invention, including embodiments or designs that may not be specifically described or illustrated herein.

Figure 11:
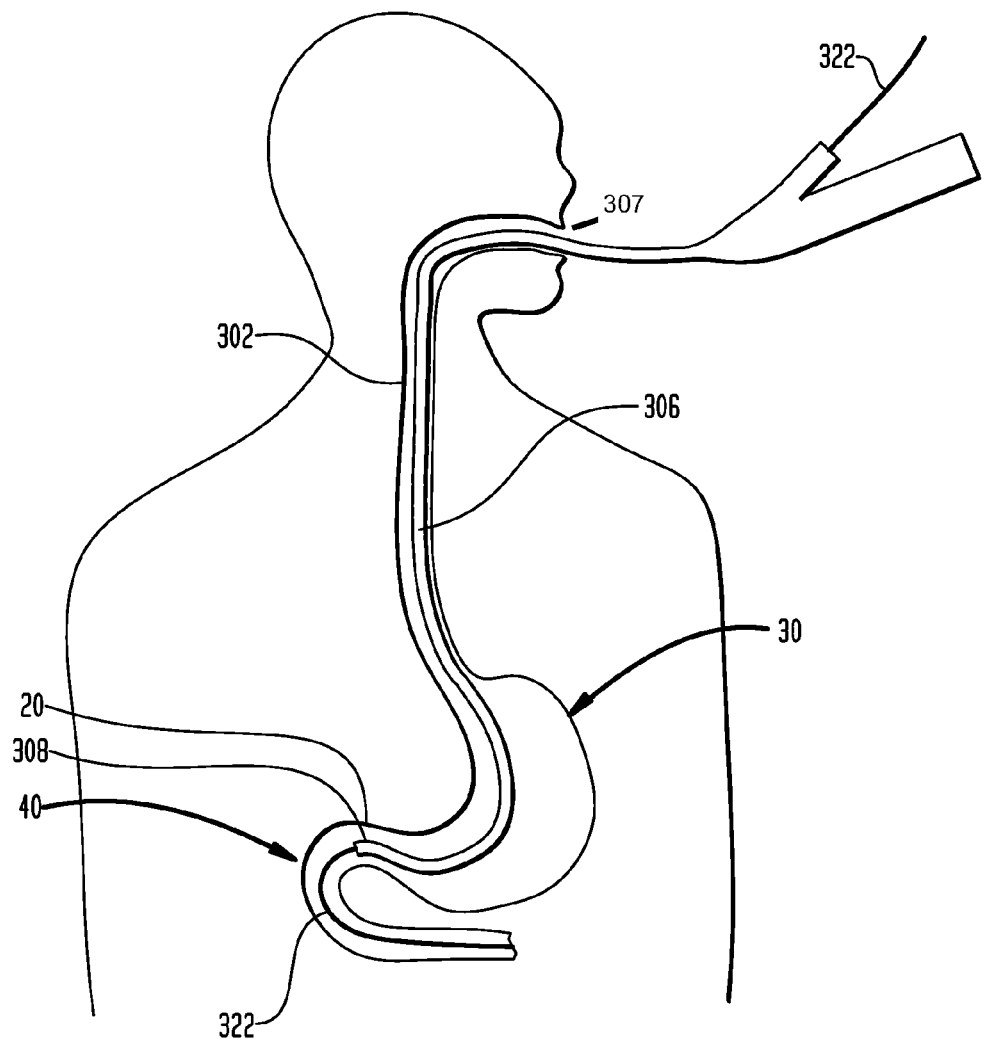
FIG. 11 illustrates the insertion of a gastroscope and guidewire through an esophagus of a patient.
Figure 15:
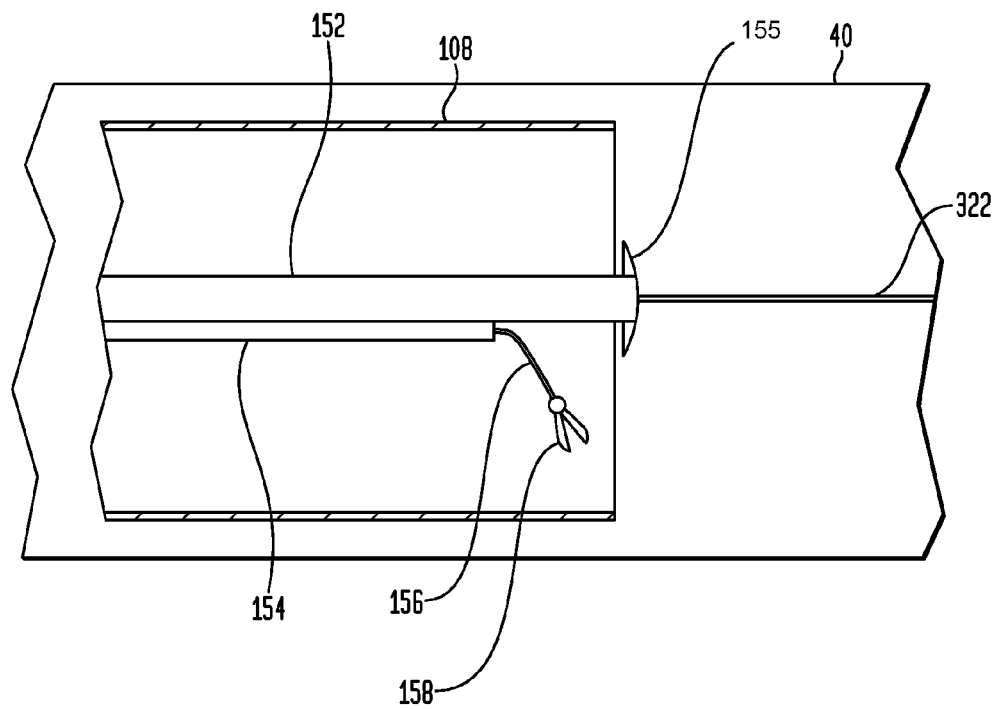
FIG. 15 illustrates the deployment of the sleeve into the small intestines of the patient.

Device 100 enters and exits the patient through esophagus 302 and is ultimately positioned in its operative state, wherein pyloric columns 106 extend through pyloric sphincter 20 (e.g., see FIG. 15). Initially, a gastroscope 306 is lubricated, inserted into patient's mouth 307, and fed through esophagus 302 and the gastroesophageal ("GE") junction 310 into stomach 320, as shown in FIG. 11. Gastroscope 306 is preferably approximately 9.8 millimeters in length, and preferably has approximately a 2.8 millimeter working channel and suitable viewing and recording equipment, for example. It will be understood that tools and components that are described as being passed through or inserted into gastroscope 306 are passed through or inserted into its working channel. A lubricant such as Surgilube or equivalent may be provided as needed to lubricate the bypass device and/or any of the associated surgical equipment.

Gastroscope 306 should ultimately be positioned such that its distal end 308 is adjacent to pyloric sphincter 20. Preferably, a guidewire 322 is hydrated and inserted through gastroscope 306. Guidewire 322 is passed through pyloric sphincter 20, which may be aided by manipulation of gastroscope 306. It may also be beneficial to pass a distal end 308 of gastroscope 306 through pyloric sphincter 20 in order to maneuver guidewire 322 through same. There should preferably be at least about 30-40 centimeters of the length of guidewire 322 passed distally through pyloric sphincter 20 and into small intestine 40 so that any further movement of guidewire 322 during the insertion procedure does not result in the accidental removal of the distal end of guidewire 322 to a position proximal of pyloric sphincter 20. Of course, the length of guidewire 322 that should preferably be passed distally through pyloric sphincter 20 may vary according to different patients and/or procedures and may be less or more than 30-40 centimeters. After guidewire 322 is appropriately positioned, gastroscope 306 is removed from the patient.

Figure 12:
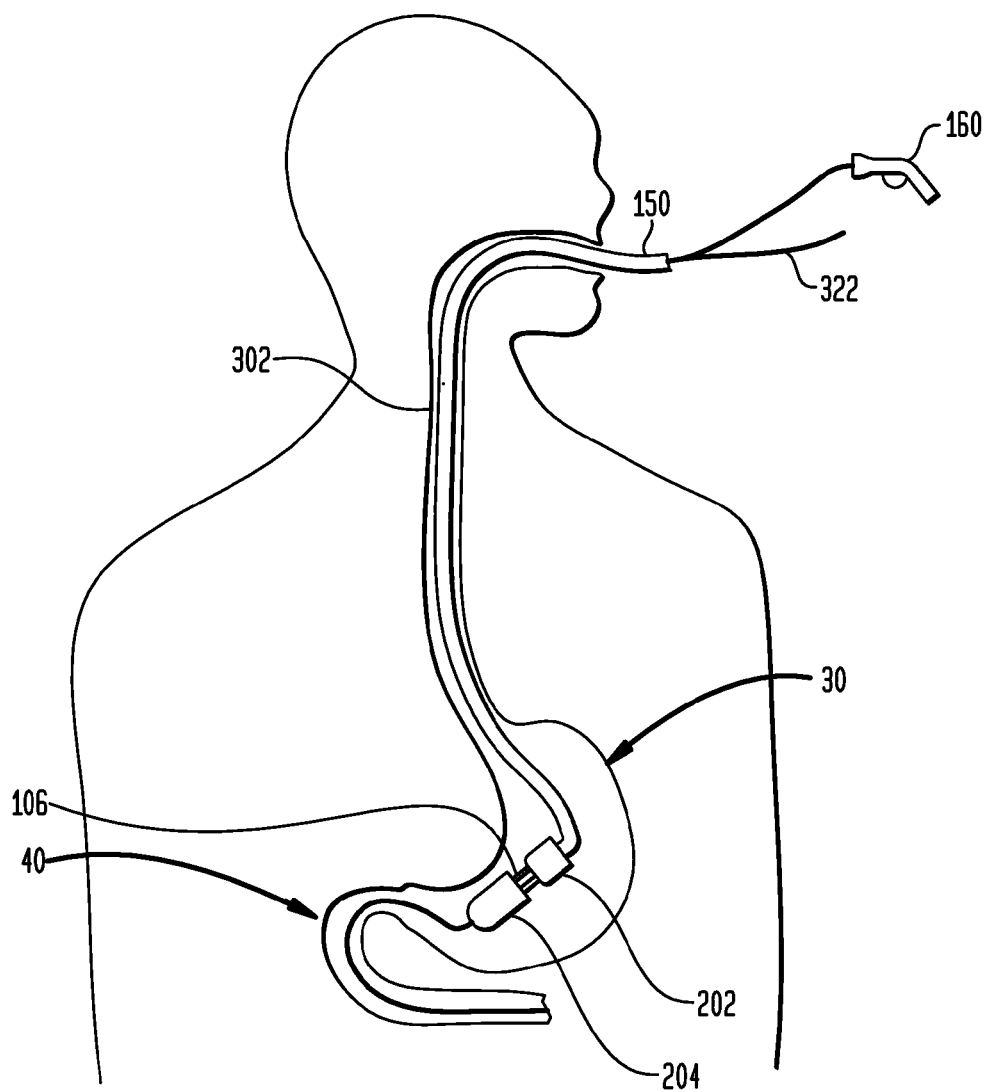
FIG. 12 illustrates the bypass device and a portion of the delivery system inserted into the stomach in the esophagus of the patient.
Figure 13:
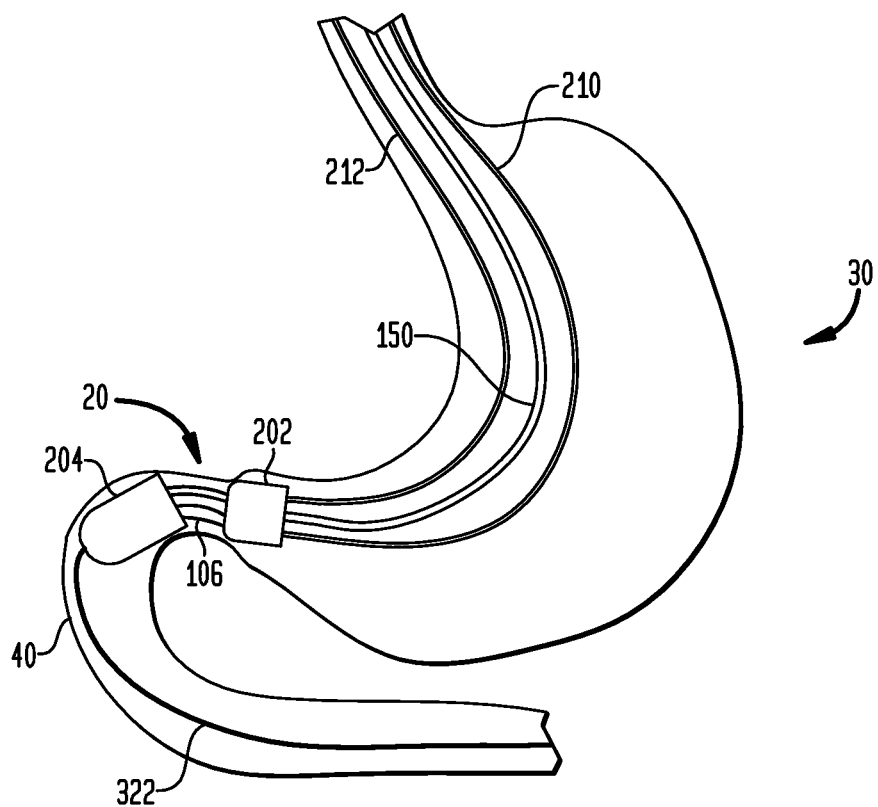
FIG. 13 illustrates the deployment of the duodenal anchor and the sleeve into the duodenum of the patient.
Figure 14:
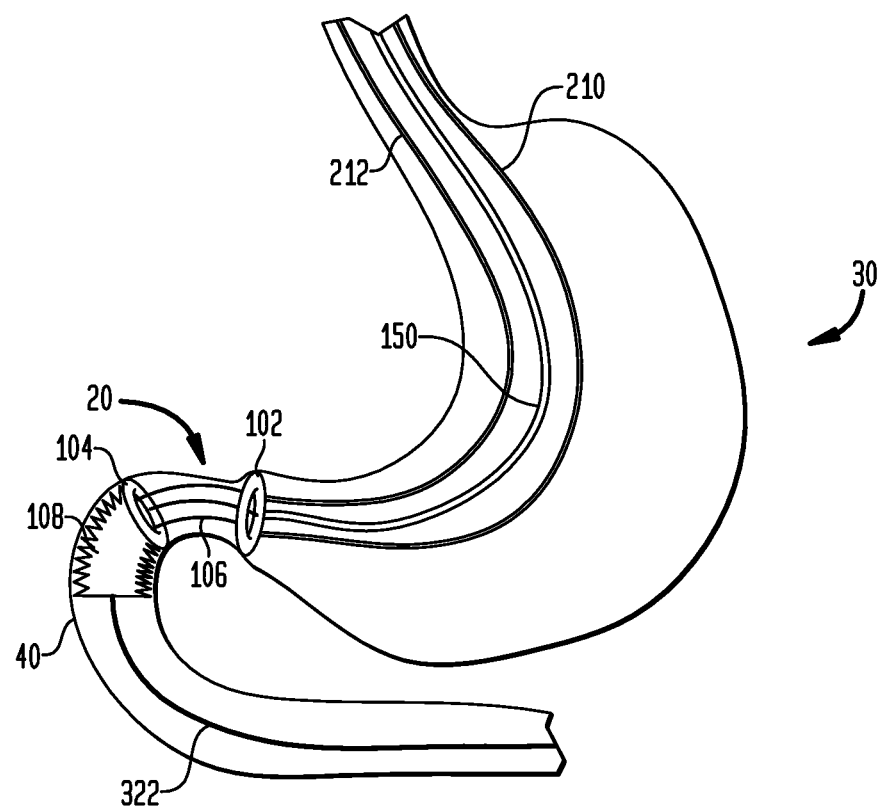
FIG. 14 illustrates the inflation of the gastric and duodenal anchors.

Referring now to FIG. 12, bypass device 100 and delivery system 200 are lubricated and positioned over the guidewire 322 outside of the patient by advancing the proximal end of guidewire 322 through hole 206 in distal capsule 204 and into the inner lumen of support tube 152 (see FIG. 10). In some embodiments, an overtube (not shown) may be positioned over the guidewire 322 and advanced through the esophagus and into the patient's stomach. The overtube typically has an inner diameter of approximately 16 mm. However, in the preferred embodiment, an overtube is not required for implantation of bypass device 100. A small steerable scope (not shown) may be advanced through the esophagus into stomach 30 through the pylorus and into the proximal portion of the duodenum. The scope is used to confirm the tissue of the stomach, pylorus and duodenum are robust and show not overt signs that they will not tolerate the device. In an exemplary embodiment, a small tube (not shown) may be inserted into the pylorus. The tube includes a distal inner tube-shaped balloon (not shown) that expands to a known diameter with a known volume of saline. In conjunction with the scope images and other prior imaging data, this instrument is used to determine the appropriate size of bypass device 100 to be used, particularly the appropriate size of duodenal anchor.

Referring now to FIG. 12, once the appropriate size bypass device 100 is selected, distal capsule 204 (containing sleeve 108 and duodenal anchor 104) and proximal capsule 202 (containing gastric anchor 102 and at least a portion of columns 106) are then advanced through the esophagus and into the stomach along guidewire 322. Once through the esophagus, distal and proximal capsules 204, 202 separate, but remain flexibly coupled together by columns 106 and fluid tube 210 (note that tubes 210, 212 are not shown in FIG. 12). The capsules 202, 204 are also still aligned with each other by virtue of delivery tube structure 150 and guidewire 322 that remain extending through the entire device 100. Once the entire device is within the stomach, support tube 152 is used to push the distal end of delivery tube structure 150 and distal capsule 204 through the pylorus into the proximal duodenum (see FIG. 13). This may require the use of a dilator (not shown) to maintain the pylorus in its maximum diameter. Alternatively, a separate pusher rod (not shown) may be used to push the distal components of bypass device 100 into stomach 30. It should be noted that it may not be necessary to encapsulate any components of device 100 in order to advance them through the patient's GI tract. In this case, these components will simply be advanced in their deflated configurations.

At this point, the surgeon will wait until capsules 202, 204 dissolve (unless capsules 202, 204 are not being used). It is expected that proximal capsule 202 will dissolve more rapidly, as it is designed to do so, and is subjected to a slightly more caustic environment within the stomach (alternatively, capsules 202, 204 may comprise material that can be excreted naturally by the patient). Once the proximal components of bypass device 100 are freed from capsule 202, a fluid, such as saline, is introduced through fluid tube 212 into the interior of inflatable member 112 until it is filled to the appropriate size (see FIG. 14). After inflating gastric anchor 102, and after distal capsule 204 has also dissolved, fluid is delivered through fluid tube 210 into the interior of inflatable member 132 of duodenal anchor 104 in a similar fashion.

Referring now to FIG. 15, once duodenal anchor 104 has been inflated into its operative configuration, sleeve 108 is advanced through the duodenum and into the jejunum to its final deployment position. Specifically, support tube 152 is used to push sleeve 108 and delivery structure 150 through the patient's small intestines. Once in final position, clamp 158 is released via the actuator device or handle outside of the patient (not shown) to disengage it from the distal end of sleeve 108.

In an alternative embodiment, the surgeon will not wait until distal capsule 204 is dissolved before advancing sleeve 108 to its final deployment position in the small intestines. In this embodiment, once capsule 204 has been advanced through the pylorus into the proximal duodenum, gastric anchor 102 is inflated as discussed above. Capsule 204 is then advanced further into the duodenum until duodenal anchor 104 is forced out of the proximal opening of capsule 204 (anchor 104 will be prevented from further distal movement by gastric anchor 102). Capsule 204 will then be advanced through the duodenum until the distal end of sleeve 108 reaches its final deployment position. Clamp 158 is then disengaged from sleeve 108 and removed from the patient as described above and capsule 204 will eventually dissolve.

Figure 16:
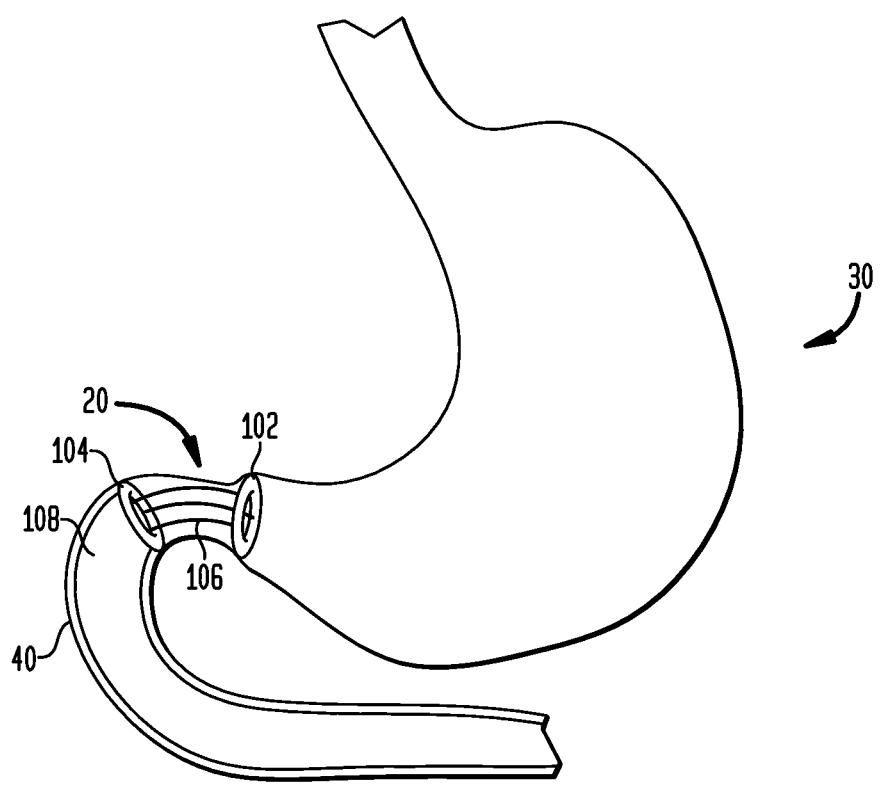
FIG. 16 illustrates the bypass device in place in its operative configuration in the patient.

As shown in FIG. 16, bypass device 100 should now be in its final position with gastric anchor 102 in pyloric antrum 340 of stomach 30 and duodenal anchor 104 just distal to the pyloric sphincter 20. Delivery structure 150 is removed from the patient and the distal end of fluid tubes 210, 212 are cut with scissors or the like and removed. A gastroscope and/or fluoroscope (not shown) may be used to confirm the final placement of device 100. Once device 100 is in place, guidewire 322 can be also removed from the patient.

A method for removing bypass device 100 according to the present invention will now be described. A gastroscope may be advanced through the esophagus and into the stomach 30 of patient in a suitable position for the surgeon to view the procedure. A sharp instrument (not shown) such as scissors or the like, is advanced through the patient's esophagus into stomach 30. The sharp instrument is used to puncture gastric anchor 102 such that the fluid within the interior of membrane 112 exits into the stomach to deflate anchor 102. Alternatively, a syringe or similar suction device (not shown) may be attached to the valve inlet 120 to withdraw the fluid from gastric anchor 102.

Once deflated, gastric anchor is preferably positioned to the side of antrum 340. A grasping or cutting instrument (not shown) is advanced through the esophagus to cut each of the pyloric columns 106 to detach gastric anchor 102 from the distal portion of device 100. The last column 106 that is severed will be held by the grasping instrument to ensure that duodenal anchor 104 and sleeve 108 do not migrate in the distal direction after being detached from gastric anchor. At this point, a grasping tool or snare (not shown) is advanced into stomach 30 to grab gastric anchor 102 and gastric anchor 102 is then pulled through the esophagus and removed from the patient.

The sharp cutting instrument is then advanced through the pyloric sphincter 20 to puncture membrane 132 of duodenal anchor 104 to deflate duodenal anchor 104. The grasping instrument may then be used to pull anchor 104 and sleeve 108 into stomach 30. Once duodenal anchor 104 and sleeve 108 are within stomach 30, they may be sliced up and removed or removed as a single unit. Subsequent to the removal of device 100, a scope (not shown) can be used to determine if any tissue injury or insult that has been sustained by the implantation, use, or removal of device 100. Provided no additional access to the stomach, pylorus, or duodenum is required, removal of the scope concludes the procedure.

Alternatively, the duodenal anchor 104 can be deflated without severing columns 106 and removing gastric anchor 102. In this embodiment, the sharp instrument is advanced around gastric anchor 102, through columns 106 and pylorus 20 to duodenal anchor 104. Duodenal anchor is deflated and pulled into the stomach (along with sleeve 108). The entire bypass device 100 may then be removed as a single unit, or it may be sliced up into smaller components to facilitate passage through the patient's esophagus.

Figure 17:
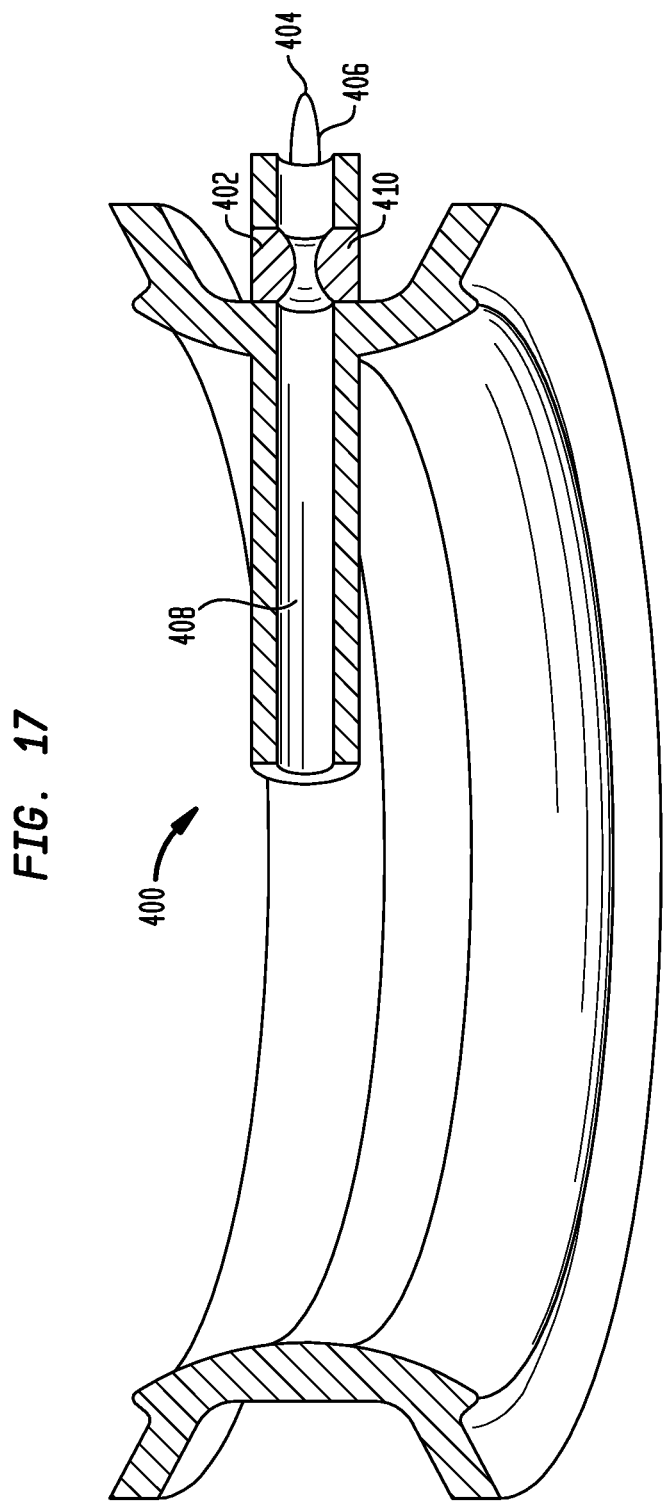
FIG. 17 is a partial cross-sectional view of an alternative embodiment of a valve for the duodenal and gastric anchors of the bypass device.

FIG. 17 illustrates one portion of an alternative embodiment of the gastric and duodenal anchors (for convenience only one of the anchors is shown in FIG. 17). In this embodiment, the anchors both include an outer wall housing a hollow interior designed for inflation as described above. FIG. 17 illustrates a central portion 400 of the outer wall of the anchors. As shown, the anchors further include a valve 402 having an inlet 404, a one-way valve member 406, a fluid passage 408 and an expandable member 410 located within fluid passage 408 between the interior of the anchor and valve member 406. Expandable member 410 preferably comprises a material designed to slowly absorb fluid upon, such as water or saline and expand with the absorbed fluid. In the preferred embodiment, expandable member 440 comprises a hydrogel material although other materials can be used that are well known in the art.

To inflate the anchor, fluid is delivered through inlet 404 such that it passes via fluid passage 408 past expandable member 410 and valve member 406 into the interior of the anchor. Valve member 406 is designed to prevent the fluid from flowing back through fluid passage 408 and inlet 404. As additional protection from this event occurring, however, expandable member 410 will absorb fluid as the fluid fills the interior of the anchor and passes back through passage 408 to saturate expandable member 410. Expandable member 410 is designed to expand when hydrated such that it completely blocks fluid passage 408, thereby preventing any fluid flow in either direction through fluid passage. This not only provides additional protection from fluid leakage, but also prevents any unwanted fluid (such as stomach acid and the like) from passing into the interior of the anchor.

Figure 18:
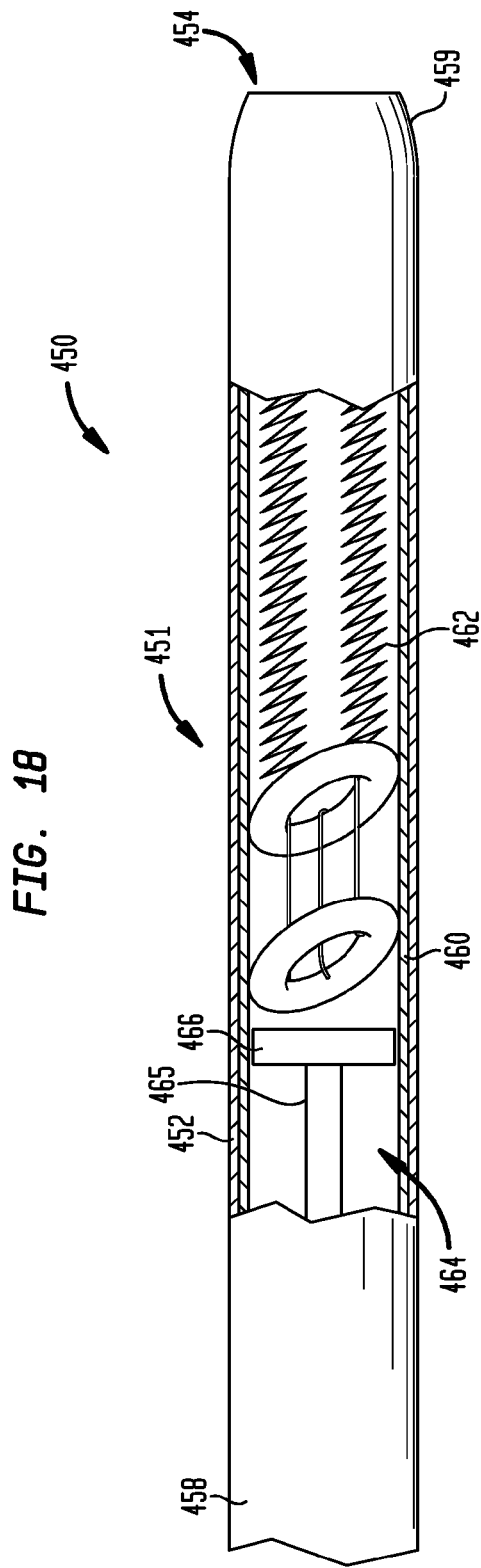
FIG. 18 illustrates an alternative introducer tube for the delivery system of the present invention.

FIG. 18 illustrates an alternative embodiment of a delivery system 450 of the present invention. In this embodiment, system 450 comprises an introducer tube 451 defining an elongate shaft 452 that has sufficient flexibility to extend through a patient's esophagus into the stomach (similar to the overtube described above). Shaft 452 has an open distal end 454 and an open proximal end (not shown as the entire shaft 452 of tube 451 is not shown in FIG. 18) and an internal lumen 458 designed as a working channel for passing instruments therethrough. Tube 451 further comprises a thin flexible bag or sleeve 460 comprising a suitable biocompatible material such as silicone or the like. Sleeve 460 houses a bypass device 462 such as one of the bypass devices described above. Sleeve 460 is preferably long enough to extend entirely through internal lumen 458 of shaft 452 to facilitate placement of sleeve 460 and device 462 in tube 451 (see below). In the preferred embodiment, sleeve 460 has open distal and proximal ends and is fastened to the proximal end of introducer tube 451 such that sleeve 460 remains within tube 451 when device 462 is propelled from tube 451 (see below). Sleeve 460 is also sized to allow it to fit within internal lumen 458 while still housing bypass device 462 in its collapsed configuration.

System 450 may optionally include a pusher or advancing member 464 including an elongate rod 465 with a proximal handle (not shown) and a distal pusher 466 designed to press against a proximal end of bypass device 462 when bypass device 462 is loaded within lumen 458 of tube 451. In some embodiments, handle 467 can be used to collapse or expand pusher 466 (discussed below). Tube 451 further comprises a tapered distal end 459 around distal opening 454 to provide for atraumatic advancement through the esophagus.

In use, bypass device 462 is placed within sleeve 460 and sleeve 460 is loaded into the distal end portion of internal lumen 458. In a preferred embodiment, the user extends the proximal end of sleeve 460 through the entire length of lumen 458 and pulls sleeve 460 proximally such that bypass device 462 is pulled into the distal end portion of lumen 458. Once loaded, the device 462 is ready for implantation in the patient.

To implant the device, introducer tube 451 is extended through the patient's esophagus such that its proximal opening 454 is positioned within the stomach. Bypass device 462 is then propelled out of tube 451 into the stomach. This can be accomplished by passing advancing member 464 through proximal opening 456 of introducer tube 451 and advancing it through lumen 458 until it propels bypass device 462 out of the distal opening 454 of tube 451. Alternatively, other devices, such as a gastroscope, can be used to propel bypass device into the stomach.

In the preferred embodiment, sleeve 460 has open proximal and distal ends and is designed to remain within lumen 458 of tube 451 as bypass device 462 is advanced into the stomach. Thus, both sleeve 462 and tube 451 can be easily removed from the patient after device 462 has been deployed. In other embodiments, sleeve 462 passes into the stomach along with device 462 and is then detached or removed from device 462. This can be accomplished by a variety of means, such as cutting the sleeve away from the device 462. Alternatively, sleeve 462 may already include a cut-a-way portion that can be easily detached to open sleeve 462 and allow bypass device 462 to be removed. In yet another embodiment, sleeve 462 may comprise a dissolvable material that dissolves away within the stomach (similar to the capsules discussed above). Once it has been deployed into the stomach, bypass device 462 may be passed along a guidewire and deployed into its final position as discussed above.

In certain embodiments, introducer tube 451 is long enough to extend through the esophagus and stomach and through the pylorus into the duodenum of the patient. In these embodiments, tube 451 may optionally include a bend at its distal end portion to facilitate passage of the tube 451 through the natural bend in the human stomach between the esophagus and the pylorus. Alternatively, the delivery system may include a separate overtube having such a bend. In this embodiment, the separate overtube will be first inserted through the esophagus with a separate straight introducer therein (i.e., to maintain the overtube in a substantially straight configuration as it passes through the esophagus). Once the overtube has passed through the esophagus, the straight introducer is removed such that the overtube is allowed to bend within the stomach into its natural position. At that point, the flexible introducer tube 451 housing the bypass device is advanced through the overtube to the duodenum.

In use, once the distal opening of tube 451 resides in the duodenum, the distal end portions (i.e., the sleeve and the duodenal anchor) of the bypass device are propelled out of the distal opening of the introducer tube 451 and into the duodenum of the patient. The duodenal anchor is then inflated to prevent proximal movement of the distal end portions of the bypass device. The introducer tube 451 is then retracted through the pylorus and into the stomach. As this occurs, the gastric anchor will naturally be pulled out of the distal end of the introducer tube 451 from the counterforce of the inflated duodenal anchor against the distal surface of the pylorus. The gastric anchor may then be inflated within the stomach and the sleeve extended through the duodenum as described above.

In yet another alternative embodiment, the pusher device or advancing member is designed to perform multiple functions. Namely, the pusher device is sized and shaped to fit between the gastric and duodenal anchors within the introducer tube. In this capacity, the pusher device is used to push or propel duodenal anchor and sleeve out of the distal opening of the introducer tube into the duodenum. In addition, the pusher device will function to prevent the gastric anchor from being advanced through such distal opening when the distal opening is located within the duodenum. Once the distal opening of the introducer tube has been retracted through the pylorus into the stomach, the pusher device is designed to collapse and retract proximally through the middle of the gastric anchor. It can then be expanded again to propel the gastric anchor through the distal opening of the introducer tube and into the patient's stomach.

In one embodiment, the pusher device comprises an elongate rod coupled to an umbrella-shaped or claw-shaped proximal pushing device. The rod is sized to extend through the introducer tube and through the center of the gastric anchor. The proximal pushing device is sized to reside between the gastric and duodenal anchors. Distal advancement of the rod will cause the pusher device to propel the duodenal anchor through the distal opening of the introducer tube. The pusher device further comprises an actuator at the proximal end of the rod for collapsing the umbrella-shaped pushing device such that it can be retracted proximally through the center of the gastric anchor. The actuator can then be used to expand the pushing device such that further distal advancement of the rod will cause the pusher device to propel the gastric anchor through the distal opening in the introducer tube.

In yet another embodiment, an alternative method for implanting and removing the bypass devices of the present invention is now described. In this embodiment, the hollow sleeve includes one or more projections at its distal end designed to allow an endoscopic forceps, clips, clamp or similar device to attach to the projections. The projections can be loops, strings, protuberances or the like and are preferably made of the same material as the sleeve (such as silicone). The gastric and/or duodenal anchors may also include such projections for similar purposes.

In use, the bypass device is attached to an endoscopic scope by passing an endoscopic forceps or clamping device through the working channel of the scope and attaching the forceps to the projections on the distal end of the sleeve. The physician may then attach the remainder of the bypass device to the outer surface of the scope with a shroud, sleeve or other fastening device or just simply align the bypass device with the shaft of the scope. Alternatively, the scope may be advanced through the center of the two anchors of the bypass device and the sleeve such that the entire bypass device is positioned around the scope. The scope is advanced with the distal end of the sleeve through the patient's esophagus and stomach and through the pylorus into the duodenum. The remainder of the sleeve and the anchors of the bypass device are thereby pulled into the stomach alongside the scope.

Alternatively, the physician may attach the forceps to the projections on either the gastric or duodenal anchor and advance those portions of the implant through the esophagus first (i.e., passing the device into the stomach backwards). In this embodiment, the physician may then detach the forceps from the bypass device, remove the scope and attach the forceps to the distal end of the sleeve to advance the remainder of the sleeve into the patient's stomach. To avoid retraction of the anchors back through the esophagus, the gastric anchor may be fully or partially inflated after the forceps have been detached from the anchor and before withdrawing the scope through the esophagus.

After the anchors have been advanced into the stomach of the patient, the gastric anchor is preferably either partially or fully inflated as described above to prevent movement of the gastric anchor through the pylorus into the duodenum or through the lower esophageal sphincter into the esophagus. The physician then continues to advance the scope and the distal end of the sleeve through the duodenum to a position near the final target site within the patient's intestines (either in the distal duodenum or the proximal jejunum). At this point, the physician may detach the forceps from the distal end of the sleeve and withdraw the scope and forceps back into the patient's stomach.

To prevent the sleeve from "following" the scope proximally into the stomach, the physician will preferably temporarily fixate the sleeve within the duodenum. According to the present invention, one method of temporarily fixating the sleeve is to use a detachable clip (rather than the forceps described above) to grab the projection on the distal end of the sleeve. Once in position within the duodenum, the clip is opened and attached to mucosal tissue within the duodenum. The clip can then be deployed such that it is no longer attached to its shaft, but instead fastens the sleeve to the mucosal tissue on the inner wall of the intestines. This allows the scope and shaft of the clip device to be withdrawn while the sleeve is fixated within the duodenum.

In certain embodiments, multiple clips may be used to fasten the sleeve to the inner walls of the intestines. The clips may serve the purpose of creating an additional anchor for the device to prevent migration and to ensure that the sleeve remains patent during the period of time it is implanted within the patient. In addition, the clips will preferably be observable under fluoroscopy such that the physician can ensure that the sleeve has remained in place after implantation.

In another embodiment, the sleeve comprises one or more internal lumens extending down a portion of, or the entire length of, the sleeve. The internal lumens are preferably fluidly coupled to one of the flexible columns which are, in turn, fluidly coupled to a valve within the gastric anchor. In an exemplary embodiment, the sleeve will comprise 3 or 4 internal lumens spaced around its circumference. In use, a fluid is delivered through the gastric anchor and column and into the internal lumens of the sleeve. The fluid causes the sleeve to extend fully and inhibits proximal migration of the sleeve when the scope is retracted from the patient's duodenum. In addition, the fluid-filled lumens will ensure that the sleeve remains patent without any kinks or twists along its length.

Once the scope has been retracted from the duodenum, the duodenal anchor is advanced past the patient's pylorus into the proximal portion of the duodenum. Preferably, the scope is used to push the duodenal anchor through the pylorus. Alternatively, the forceps can be attached to one of the projections on either of the gastric or duodenal anchors to push and/or pull the duodenal anchor into position. The duodenal anchor is then inflated as described above.

In yet another alternative embodiment, the sleeve is "self-deploying" through the duodenum. In this embodiment, the sleeve is positioned within the proximal duodenum as described above and then allowed to "self-deploy" and advance through the duodenum into position. In one embodiment, the sleeve comprises internal fluid lumens as described above and the fluid is delivered into the lumens to force the sleeve to extend down the length of the duodenum. In another embodiment, the sleeve comprises a mass at its distal end (e.g., a thickened annular portion of the sleeve, one or more balls or projections attached to the distal end or the like). The mass will advance through the patient's intestines through natural peristalsis and pull the sleeve distally until it is fully extended. In yet another embodiment, the sleeve comprises a dissolvable portion at its distal end that occludes all or a portion of the distal end of the sleeve. In this embodiment, fluid is flushed through the sleeve and because its distal end is occluded causes the sleeve to extend distally. After the dissolvable portion dissolves within the intestines, the distal end of the sleeve is opened up to allow chyme to pass therethrough.

FIG. 19 illustrates another embodiment of the present invention. As shown, a bypass device 500 comprises a substantially hollow sleeve 502 having proximal and distal end portions 504, 506 and a gastric anchor 508 coupled to the proximal end portion 504 of sleeve 502 by a plurality of columns 510. Gastric anchor 508 may be substantially the same anchor that has been described above in previous embodiment. Proximal end portion 504 preferably comprises a funnel-shaped support member 505 designed to provide a proximal opening 507 for receiving chyme from the patient's stomach. The funnel-shaped support member 505 ensures that the proximal opening 507 remains patent and substantially oriented towards the pylorus for collecting chyme following therethrough.

In certain embodiments, proximal end portion 504 of sleeve 502 further includes a flexible expansion member 509 between support member 505 and the distal portion of sleeve 502. Expansion member 509 is primarily designed to fit within the duodenal bulb of the patient to provide additional inhibition of proximal migration of the device through the patient's pylorus. In the exemplary embodiment, expansion member 509 has a substantially spherical shape and includes one or more cut-a-ways to allow expansion member to expand and contract upon itself under the forces of peristalsis.

In other embodiments, flexible expansion member 509 comprises an expandable anchor device similar to the duodenal anchor described above. In yet other embodiments, proximal end portion 509 comprises a smaller inflatable toroid member that provides structure and some resistance to proximal migration of sleeve 502 through the patient's pylorus, but has a smaller diameter in the inflated configuration than the maximum diameter of the pylorus. In these embodiments, proximal end portion 504 is easier to advance through the pylorus during implantation.

Distal end portion 506 preferably comprises a plurality of elastomeric objects 512 extending from the distal end of sleeve 502. Objects 512 are designed to hang freely from sleeve 502 to provide a distal anchor or weight for sleeve 502 within duodenum. Objects 512 are preferably designed to exert a pull force on sleeve 502 in the distal direction during the natural peristalsis in the patient's GI tract to thereby pull objects 512 (and sleeve 502 therewith) distally. This ensures that sleeve 502 remains within the duodenum. In an exemplary embodiment, objects 512 comprise a series of ball-shaped silicone members that are coupled together along a thin flexible elongate member 514 extending distally from sleeve 502. Elongate member 514 may also comprise silicone and has a proximal end coupled to the distal end of sleeve 502 and extends distal of sleeve into the duodenum.

Sleeve 502 preferably has a length sufficient to allow chyme passing from the stomach through pylorus to bypass a selected length of the duodenum such that the chyme does not contact the walls of the duodenum over the selected length. As discussed in detail above, this inhibits caloric absorption in the selected length of the duodenum to provide weight loss and inhibits certain hormonal triggers in the duodenum that may cause insulin resistance in a patient. Applicant has made the surprising discovery that in certain instances the sleeve 502 may only need to bypass the proximal portion of the duodenum in order to achieve these effects. Thus, in certain embodiments the sleeve 502 is only long enough to extend from the duodenal bulb to a point just distal of the sphincter of Oddi (i.e., about 2-10 inches; preferably about 3-5 inches in length).

Figure 20:
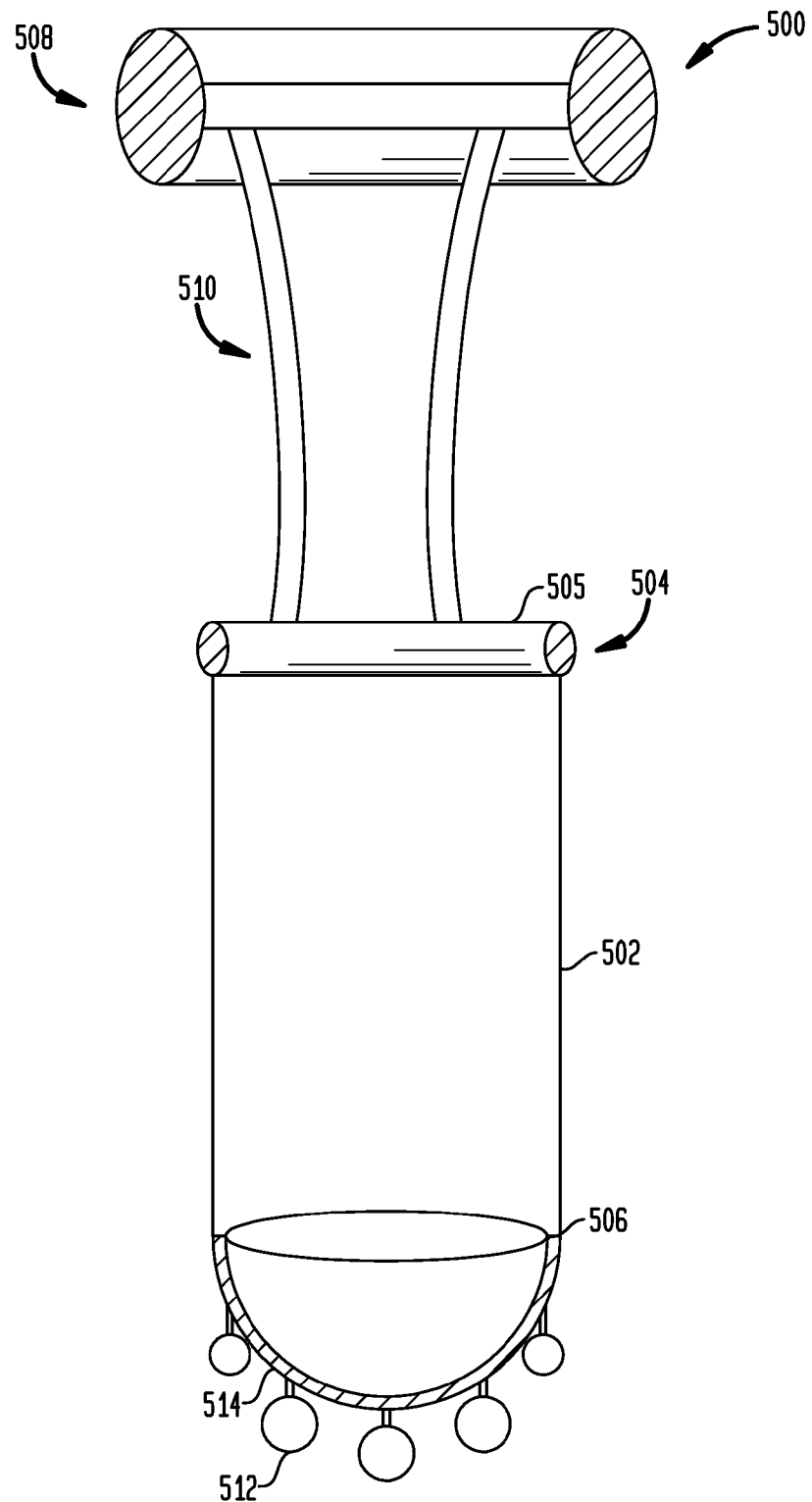
FIG. 20 illustrates yet another alternative embodiment of a bypass device according to the present invention.

FIG. 20 illustrates another embodiment. As shown, proximal end portion 504 of sleeve 502 comprises an annular support ring 505 that provides structure to sleeve 502 at its proximal end and couples sleeve 502 to columns 510. In other embodiments, proximal end portion 504 is a solid ring member that does not inflate. In yet other embodiments, bypass device 500 does not have a proximal end portion 504. In such embodiments, columns 510 attached directly to the proximal end of sleeve 502.

In the FIG. 20 embodiment, objects 512 and elongate member 514 preferably extend in a loop from one side of the distal end of sleeve 502 to the other. This configuration acts as a pull-weight to pull sleeve 502 in the distal direction along GI tract. Gastric anchor 508 then acts as a counterbalance to this pulling force to maintain the device in place. Elongate member 514 preferably has a length of between about 5 to 40 mm and ball-shaped elements 512 preferably have diameters of between about 1 to 10 mm.

Of course it will be recognized that other configurations are possible. For example, objects 512 may extend around the distal end of sleeve 502 in an annular or ring shape. Alternatively, sleeve 502 may comprise a single ball attached to the center of an elongate member extending from one side of the distal end of sleeve to the other. In this configuration, the single ball member may be slightly larger in diameter than the individual ball members 512 shown in FIG. 19. In addition, it should be noted that solid members 512 may have a variety of different shapes (other than spherical) such as conical, square, rectangular, toroidal or the like.

In an alternative embodiment, device 500 will not include objects 512 or elongate member 514. Instead, sleeve 502 will have a distal end portion that has more mass/weight than the sleeve 502 itself to provide a pull force on sleeve 502 through natural peristalsis. In one such embodiment, sleeve 502 includes an annular ring (not shown) at its distal end that can be made of, for example, a thicker silicone member attached to or an integral part of the sleeve 502. In another embodiment, sleeve 502 may include an expandable or inflatable distal end portion.

In yet another embodiment, a system and method for generating a pull force from a patient's anus to the mouth is described. In certain circumstances, it may be difficult to directly access a target location in certain distal portions of a patient's intestines with an endoscopic approach through the patient's mouth and esophagus. In particular, a patient's anatomy may make it difficult to advance a scope distally beyond the second or third portion of the duodenum. In other cases, the physician may be capable of advancing the scope to the target location, but may not be capable of translating a push or pull force at the tip of the scope sufficient to advance another object (e.g., the bypass device described above).

To obviate the above issue, the present invention includes a system and method for allowing an object to be pulled distally through at least a portion of the GI tract by exerting a pull force from the patient's anus. In one embodiment, the system comprises an object (such as a silicone ball) attached to the distal end of a long flexible member (such as a string or suture). The object has a sufficient weight and/or mass to allow peristalsis to carry said object through the patient's intestines and comprises a material that will inhibit the object from being eroded by the natural erosion forces within the intestines. The long flexible member preferably has a length sufficient to extend from a patient's mouth through the entire GI tract and the anus.

In use, the object or ball member is swallowed by the patient and allowed to advance through the GI tract through natural peristalsis until it exits the anus. The proximal end of the flexible member is held outside of the patient's mouth such that it extends through the entire GI tract. The proximal end of the flexible member is then attached to the object or instrument that it is desired to advance to the target location. The ball member can then be pulled on to pull the object through the esophagus, stomach and intestines to the target location. The physician may follow the object with an endoscope to ensure proper placement. Once in the target location, the object is detached from the flexible member (via endoscopic scissors or the like or via a wireless switch attached to the flexible member and object that can be actuated from outside of the patient's body) and the flexible member is pulled completely through the GI tract and removed from the patient.

In certain instances, the patient's intestines may be too flexible to allow the physician to exert a sufficient pull-force on the object with the flexible member. In other words, pulling on the flexible member may simply cause the flexible member and the intestines to bend or otherwise move such that the pull force is not translated to the object. To obviate this, the present invention further includes a tube having an internal lumen sized for receiving the flexible member. The tube preferably comprises a material flexible enough to pass through the entire GI tract and rigid enough to inhibit significant bending or lateral movement of the flexible member when a pull force is exerted on the flexible member. Thus, as the flexible member is pulled in a distal direction through the GI tract, the tube will provide sufficient rigidity to allow the object to be pulled therewith. The tube will also have a length sufficient to extend from at least the patient's pylorus to the anus and preferably from the mouth to the anus. The tube is preferably detachably coupled to the ball member such that the tube is advanced through the GI tract along with the ball member through natural peristalsis, but can then be detached after it passes through the anus such that the flexible member can be pulled independently from the tube.

In use, the ball member is swallowed and advanced through the GI tract together with the flexible member and the tube through natural peristalsis. After the ball member as passed through the patient's anus, the tube can be detached from the ball member and the proximal end of the flexible member coupled to the object to be implanted. The ball member is pulled such that the string (and the object therewith) are pulled through the patient's GI tract to the target location as described above. The tube may also be partially pulled through the GI tract such that the object remains proximal to the proximal end of the tube.

Figure 21:
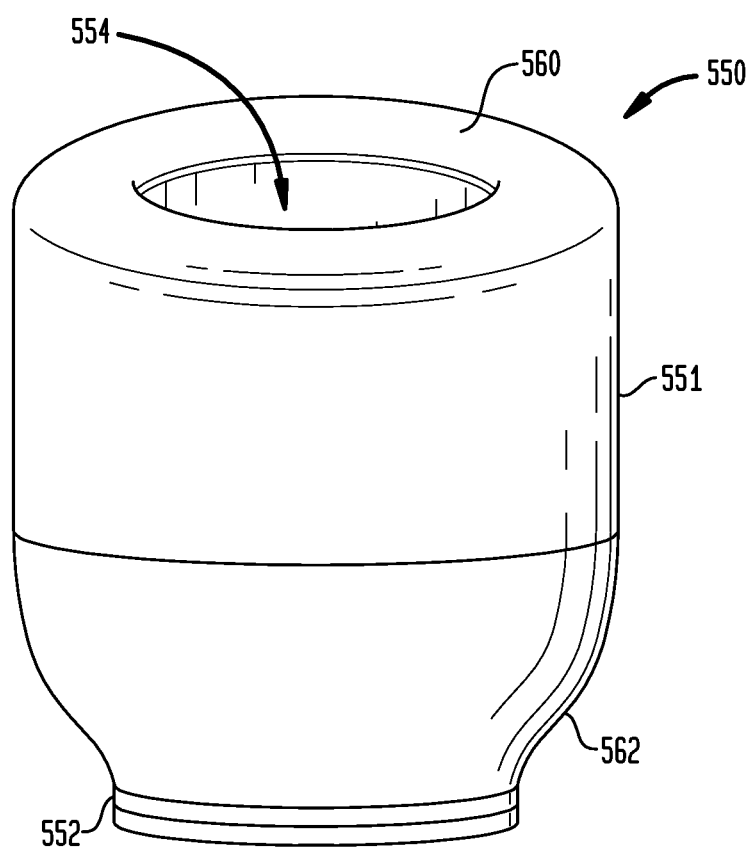
FIG. 21 is a perspective view of an alternative embodiment of a duodenal anchor according to the invention.
Figure 22:
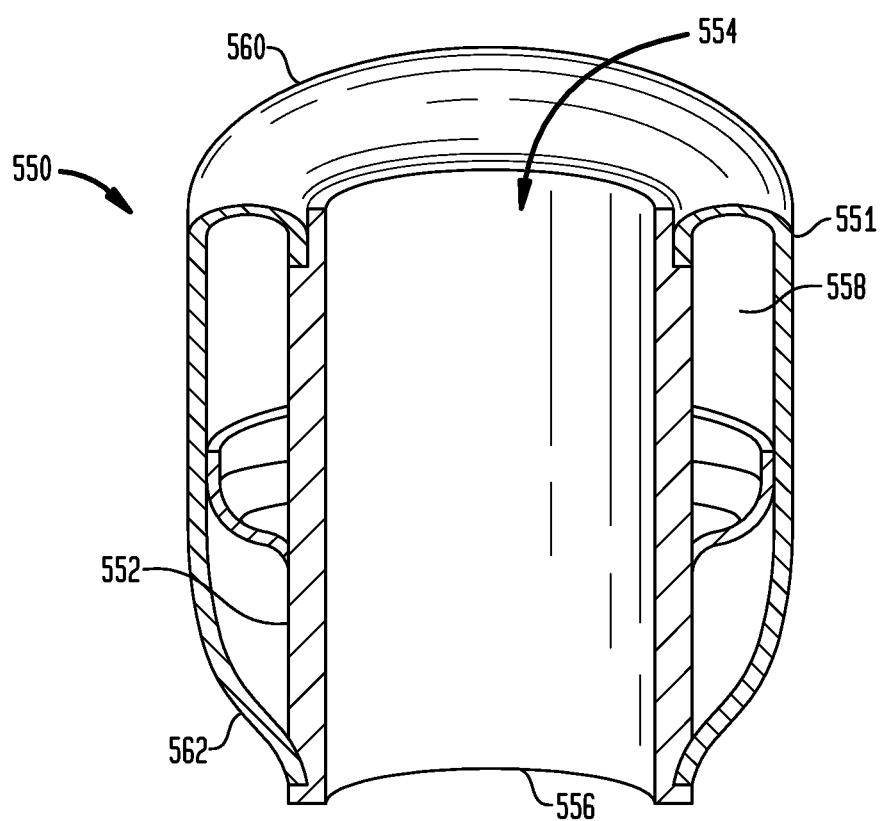
FIG. 22 is a cross-sectional view of the duodenal anchor of FIG. 21.

FIGS. 21 and 22 illustrate yet another embodiment of a duodenal anchor 550 according to the present invention. Duodenal anchor 550 may be used with any of the combinations of sleeves and gastric anchors described above. Typically, duodenal anchor 550 is coupled to a gastric anchor by one or more flexible columns or tethers (not shown). As shown, duodenal anchor 550 comprises an inflatable membrane 551 coupled to the outer wall of a central tubular support structure 552. Support structure 552 has open proximal and distal ends 554, 556 to provide a channel for flow of chyme therethrough. Support structure 552 preferably has a length or height in the longitudinal direction of about 20-40 mm, preferably about 25-35 mm, depending on the anatomy of the patient (discussed below) and an inner diameter of about 10-25 mm, preferably about 12-18 mm. Distal end 556 of support structure 552 will typically be coupled to a hollow sleeve (not shown) similar to one of the sleeves described above. In certain embodiments, support structure 552 may comprise an internal restrictor (not shown) that reduces the inner diameter of structure 552 to further restrict the flow of chyme therethrough. Similar to previous embodiments, this helps to reduce the flow rate of chyme from the patient's stomach to increase the sensation of satiety.

Support structure 552 preferably comprises the same durometer material as membrane 551 but with a larger wall thickness to thereby provide rigidity and support to membrane 551. In an exemplary embodiment, membrane 551 and support structure 552 each comprise a silicone material with a durometer of about 30-50 A and wall thicknesses of about 0.5 to 1.0 mm and 1.0 to 2.0 mm, respectively. Alternatively, support structure 552 may have the same or substantially the same wall thickness as membrane 551, but comprise a harder material than inflatable membrane 551 or a harder durometer. Exemplary materials for membrane 551 and support structure 552 are silicone, polyurethane, polyethylene, GORE-TEX®, Teflon® and the like.

Inflatable membrane 551 is coupled to the outer walls of support structure 552 and has a hollow interior 558 that can be expanded when fluid, such as saline, air, barium, hydrogel or the like, is delivered therein. Similar to previous embodiments, membrane 551 will preferably include a one-way valve (not shown) designed for coupling to an external fluid tube that allows fluid to be delivered into interior 558 of membrane 551 to expand the membrane into the configuration shown in FIGS. 21 and 22. In the expanded configuration, membrane 551 has a substantially cylindrical shape that tapers inward from the proximal end 560 to the distal end 562. In the exemplary embodiment, proximal end 560 of membrane 551 has an outer diameter of about 20-30 mm, preferably about 24-26 mm, in its natural (i.e., non-elastically expanded) configuration and distal end 562 of membrane 551 has an outer diameter of about 10-20 mm, preferably about 12-18 mm.

The size and shape of duodenal anchor 550 in the expanded configuration has a number of advantages. The substantially cylindrical shape of the support structure and inflatable membrane inhibits turning of the device within the duodenal bulb of the patient. In particular, the longitudinal size of support structure 552 is preferably longer than its diameter, thereby making it more difficult for the duodenum to turn the anchor 550 on its side. This inhibits the duodenal anchor 550 from becoming a blockage to the passage of chyme and fluids from the stomach through the small intestines. In addition, this configuration makes it more difficult for the anchor to be forced through the pylorus into the stomach by the forces exerted within the duodenum. In addition, the taper in the inflatable membrane 551 substantially conforms to the anatomy of the duodenal bulb of a patient. Thus, anchor 550 will cause less trauma to the tissue within the duodenal bulb.

Duodenal anchor 551 is configured for inflation to a size that will substantially conform to the inner diameter of the duodenal bulb within the patient's small intestines. Preferably, anchor 551 is configured for inflation to a size that will exert a slight amount of radially outward force against the duodenal wall such that anchor 551 maintains its position within the duodenal bulb without causing excessive trauma to the tissue within the duodenum. In the exemplary embodiment, anchor 551 is filled to a volume of approximately 4-16 ml of fluid, preferably about 6-12 ml.

In yet another alternative embodiment, the duodenal anchor includes a biasing mechanism for exerting a radially directed outward force against duodenal anchor such that the anchor exerts a substantially continuous outward force against the duodenal tissue. Preferably, the biasing mechanism comprises a spring or similar device that is coupled to the inside surface of a support structure or membrane. It should be noted that in this embodiment the support structure may be inflatable as described above or it may not be inflated and may instead have a funnel shape as described in the embodiment above. The biasing mechanism preferably exerts sufficient force such that the support structure or membrane presses against the inner walls of the duodenal bulb. In certain embodiments, the force will be sufficient to slowly cause the tissue in the duodenal bulb to expand outward without causing trauma to or otherwise puncturing the tissue in the duodenal bulb. In other embodiments, the force will only be sufficient to cause the support structure or membrane to engage the duodenal tissue without changing the underlying shape of the duodenal bulb.

In this embodiment, the biasing mechanism ensures that the duodenal anchor will retain a shape that will remain in place within duodenal bulb. Consequently, it may not be necessary to include a gastric anchor and corresponding pyloric columns to inhibit distal migration of duodenal anchor. Thus, in one such embodiment the bypass device comprises a duodenal anchor having a biasing mechanism coupled to a sleeve as described above. The duodenal anchor in this embodiment will serve the purpose of inhibiting both proximal and distal migration of the bypass device. The advantage of this configuration is that it is not necessary to have columns extending through the patient's pylorus. In addition, the strong forces exerted by the stomach antrum will not affect the bypass device.

Figure 23:
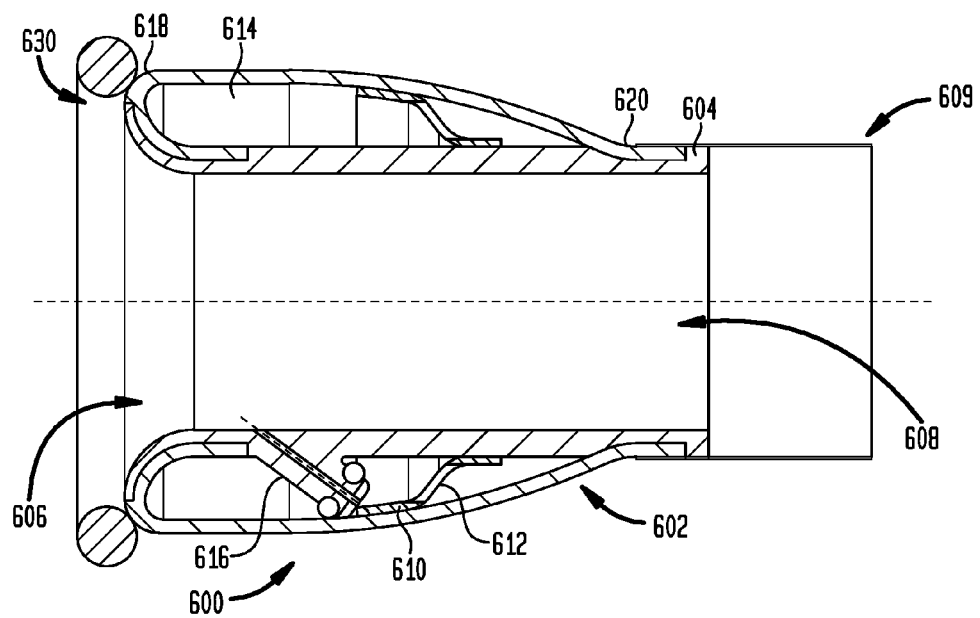
FIG. 23 is a cross-sectional view of another alternative embodiment of a duodenal anchor according to the present invention.
Figure 24:
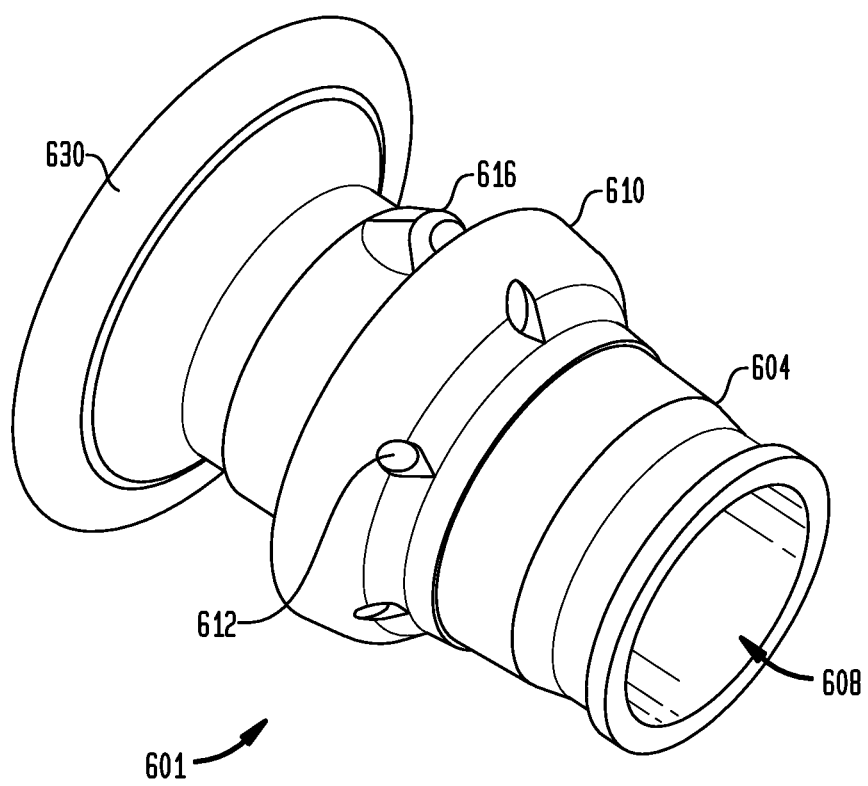
FIG. 24 is a perspective view of an internal section of the duodenal anchor of FIG. 23.

FIG. 23 illustrates yet another embodiment of a duodenal anchor 600 according to the present invention (FIG. 24 illustrates an internal portion 601 of duodenal anchor 600). Similar to the previous embodiment, duodenal anchor 600 comprises an inflatable membrane 602 coupled to the outer wall of a central tubular support structure 604. Support structure 604 has open proximal and distal ends 606, 608 to provide a channel for flow of chyme therethrough. Support structure 604 preferably has a length or height in the longitudinal direction of about 20-40 mm, preferably about 25-35 mm, depending on the anatomy of the patient (discussed below) and an inner diameter of about 10-25 mm, preferably about 12-18 mm. Distal end 608 of support structure 604 will typically be coupled to a hollow sleeve 609 (only the proximal portion of which is shown in FIG. 23) similar to one of the sleeves described above.

Also similar to the previous embodiment, support structure 604 preferably comprises the same durometer material as membrane 602 but with a larger wall thickness to thereby provide rigidity and support to membrane 602. In this embodiment, duodenal anchor 600 preferably comprises an annular internal rib 610 located between support structure 604 and membrane 602. Rib 610 provides additional stiffness and support to membrane 602 to ensure that membrane 602 can adequately resist exterior forces, such as the forces applied by the duodenal walls against the anchor 600. As shown in FIG. 24, rib 610 includes a plurality of holes 612 to allow fluid flow therebetween such that the entire interior 614 of membrane 602 can be filled with fluid.

Inflatable membrane 602 is coupled to the outer walls of support structure 604 and has a hollow interior 614 that can be expanded when fluid, such as saline, air, barium, hydrogel or the like, is delivered therein. Similar to previous embodiments, membrane 602 will preferably include a one-way valve 616 designed for coupling to an external fluid tube that allows fluid to be delivered into interior 614 of membrane 602 to expand the membrane into the configuration shown in FIGS. 23 and 24. In the expanded configuration, membrane 602 has a substantially cylindrical shape that tapers inward from the proximal end 618 to the distal end 620. In the exemplary embodiment, proximal end 618 of membrane 602 has an outer diameter of about 20-30 mm, preferably about 24-26 mm, in its natural (i.e., non-elastically expanded) configuration and distal end 620 of membrane 602 has an outer diameter of about 10-20 mm, preferably about 12-18 mm.

Duodenal anchor 600 further includes an annular ring 630 coupled to the proximal end 606 of support structure 604. Ring 630 preferably has an external diameter slightly larger than the external diameter of membrane 602 in its inflated configuration or about 25-35 mm, preferably about 28-32 mm. Ring 630 preferably has a thickness and a material selected such that ring 630 is stiffer and more resistant to forces than membrane 602, while at the same time being flexible enough such that ring 630 can be compressed into an elliptical shape such that ring 630 can be advanced through the esophagus and pylorus of the patient. In the exemplary embodiment, ring 630 comprises a silicone material having substantially the same durometer as membrane 604 and support structure 602. However, ring 630 has a thickness of about 2-5 mm, which makes ring 630 substantially stiffer than membrane 604.

Annular ring 630 provides additional support to membrane 602 within the duodenal bulb, thereby making it more difficult for the internal walls of the duodenum to squeeze anchor 600 and force anchor to migrate either distally through the duodenum or proximally the pylorus and into the patient's stomach. In addition, ring 630 modifies the overall shape of duodenal anchor 600 such that the anchor forms a proximal wedge that abuts the proximal end of duodenal bulb and/or the distal end of the pylorus.

An exemplary delivery system and method for endoscopically implanting the bypass device similar to the ones shown in FIGS. 21-24 will now be described. As shown previously in FIG. 11, the physician first advances an endoscope through the patient's esophagus and stomach and into the small intestines. A guide wire will then be advanced through the working channel of the endoscope and into the small intestines. Preferably, the guide wire is advanced to a position at least 12 inches into the small intestines and more preferably greater than 20 inches. This ensures that the guide wire will remain in place throughout the implantation process. The endoscope is then removed from the patient and the guide wire left in place.

The bypass device is then attached to the delivery device in preparation for advancing it into position within the patient. In one embodiment, the delivery device comprises a delivery tube having one or more internal lumens. The delivery tube will comprise a material (such as plastic, PTFE or the like) having sufficient rigidity to translate a push force from its proximal end to its distal end and sufficient flexibility to allow the distal end of the tube to be endoscopically advanced through the GI tract to a position about 8-15 inches into the small intestines. The tube will have a length that extends at least from the distal end of the sleeve on the bypass device to a position proximal of the duodenal anchor (with the sleeve fully extended). In certain embodiments, the tube may be longer; extending beyond the gastric anchor and/or long enough to extend through the esophagus and out of the patient's mouth with its distal end within the duodenum.

The delivery device further comprises a fastening system for securing the bypass device to the delivery tube such that the two can be advanced together into position within the patient. In one embodiment, the fastening system comprises a series of holes in the delivery tube for receiving a length of thin, flexible material, such as filament, suture, wire, twine, string or the like, therethrough. The suture is attached to the bypass device and the delivery tube through the holes to secure the device to the tube. Preferably, the tube is attached to the distal end of the sleeve to ensure that a push force from the proximal end of the tube will translate into a pull force at the distal end of the sleeve to pull the bypass device into position in the GI tract. In addition, the tube is preferably attached to the bypass device at another point either at the duodenal anchor or proximal to the duodenal anchor to ensure that the bypass device remains substantially linear with the delivery tube as the two are advanced through the GI tract. The gastric anchor may be attached to the delivery tube or it may be allowed to hang freely. Of course, the bypass device may be secured to the delivery tube at other attachment points as well. For example, it may be advantageous to bundle the duodenal anchor into a smaller configuration with suture and then attach the bundled duodenal anchor to the delivery tube.

In yet another embodiment, the fastening system comprises a separate suture tube extending along the exterior of the bypass device and the delivery tube. The suture tube will comprise a material (such as plastic, PTFE or the like) having sufficient flexibility to allow the distal end of the tube to be endoscopically advanced through the GI tract to a position about 8-15 inches into the small intestines. The tube will have a length that extends at least from the distal end of the sleeve on the bypass device to a position proximal of the duodenal anchor (with the sleeve fully extended). In certain embodiments, the tube may be longer; extending beyond the gastric anchor and/or long enough to extend through the esophagus and out of the patient's mouth with its distal end within the duodenum. The suture tube may be attached to the delivery tube (e.g., with suture or the like) at points proximal to the gastric anchor to ensure that the suture tube and delivery tube travel together as the whole system is advanced through the patient's GI tract.

The delivery device preferably further comprises a detaching system for detaching the bypass device from the delivery tube after the bypass device has been advanced into position within the patient. The detaching system is preferably designed such that the device can be detached from the delivery tube by operation outside of the patient. In one embodiment, the detaching system comprises an elongate wire or tube that extends through a lumen within the delivery tube or the suture tube. The elongate wire preferably has a handle at its distal end and a sharp distal edge, cutter or hook on its distal end designed to cut the suture within the suture or delivery tubes. In use, the elongate wire is translated with respect to the delivery or suture tubes (e.g. pulled proximally) such that the sharp distal end cuts each of the sutures passing through the holes in the delivery or suture tubes. Once cut, the sutures are free to pass through the holes such that the bypass device is detached from both the delivery and suture tubes. In another embodiment, the detaching system comprises an elongate wire coupled to one or more rods extending through a lumen within the delivery or suture tube. The rods each have a distal end and a diameter sized to receive a loop of each of the sutures. The elongate wire can be pulled to thereby pull the rods proximally until the loops of suture pass over the distal end of the rods, thereby disengaging the suture loops from the rods so that the suture is free and the bypass device becomes detached from the delivery tube.

In yet another embodiment, the suture tube comprises a series of attachment points for the suture. The attachment points comprise one or more holes for passing a loop of the suture therethrough. A pull wire passes through an internal lumen of the suture tube such that it extends through the loops in each of the sutures. Once the pull wire has been advanced distally through the internal lumen of the suture tube such that each of the suture loops are fastened within the suture tube by the pull wire, the open ends of the sutures are then tied around the delivery tube and the device. This fastens both the delivery tube and the device to the suture tube at each of the attachment points. As the pull wire is pulled proximally, it releases each of the suture loops thereby releasing the device and the delivery tube from the suture tube. In an exemplary embodiment, the attachment points comprise metal spacers having holes therein for receiving the suture loops. Of course, it will be recognized by those skilled in the art that a variety of other devices may be used to suitably detach the device from the delivery tube.

The sleeve may be fastened to the delivery tube in its fully elongated state (i.e., 2-24 inches depending on the length of the sleeve). Alternatively, the sleeve may be shortened in an accordion style such that the length from the distal end of the sleeve to the duodenal anchor is less than the fully elongated length. Since the delivery tube is at least semi-rigid and is attached to the distal end of the sleeve and the bypass device at a proximal point, the sleeve will remain in this shortened configuration during advancement of the device through the GI tract.

In the preferred embodiment, the bypass device is fastened to the delivery tube such that the delivery tube is adjacent to (or on the side of) the bypass device. Alternatively, the delivery tube may pass through the center of the bypass device (i.e., through the center of the gastric anchor and/or the duodenal anchor and the sleeve) and the suture tube will be fastened to the side of the device. In either embodiment, the delivery and/or suture tube(s) will be fastened to the bypass device so as to create a single package that can advance through the GI tract of the patient.

Once the bypass device is fastened to the delivery and/or suture tube(s), the proximal end of the guide wire is advanced through a lumen within the delivery tube and then through the scope such that the delivery/suture tube(s) and the bypass device are positioned on the guide wire distal to the scope. The delivery/suture tube(s) and bypass device are then advanced along the guide wire with the scope following the package. The scope provides visualization of the advancement of the device and can also be used as a pusher to advance the device along the guide wire. In certain embodiments, the delivery system may further include a separate pusher device designed for placement between the proximal end of the delivery tube and distal end of the scope. The pusher may comprise a substantially rigid tube with a distal engagement device designed to engage with the proximal end of the delivery tube and/or the duodenal anchor. For example, the distal engagement device may comprise a cupped shaped member designed to partially house the proximal portion of the duodenal anchor. This provides a solid engagement with the bypass device to more effectively translate a push force to the delivery tube and the device.

The additional push force from the scope and/or the pusher device may be necessary if the proximal end of the guide wire withdraws proximally and creates guide wire "loops" within the patient's stomach based on the anatomy of an individual patient. To inhibit such looping of the guide wire, the system may further include a guide wire with an expandable element (such as a balloon) at its distal end. The expandable element can be expanded within the patient's small intestines to prevent the guide wire from withdrawing proximally and creating loops within the stomach.

The delivery/suture tube(s) are preferably advanced into the small intestines until the duodenal anchor has passed through the pylorus and into the duodenum of the patient. The suture tube is then detached from the bypass device. As discussed above, the suture tube is preferably detached from outside of the patient's body with the detachment system. Thus, the elongate wire or tube is pulled from outside of the body to either cut through the sutures or to free the suture loops such that the sutures disengage from the delivery tube and bypass device. Once the sutures are disengaged from the bypass device, the suture tube may be removed from the patient's body. The gastric and duodenal anchors are then inflated as discussed above and the fill tubes are either cut within the body or pulled such that they automatically detach from the gastric anchor. In one embodiment, the fill tubes pass through a lumen in the delivery tube and through a side hole in the delivery tube proximal to the gastric anchor. When the fill tubes are pulled from outside of the patient's mouth, the delivery tube creates the necessary counter traction to allow the fill tube to disengage from the gastric and duodenal anchors. This allows the operator to withdraw the fill tubes from outside of the patient. The delivery tube and guide wire may then be removed from the patient.

Figure 25:
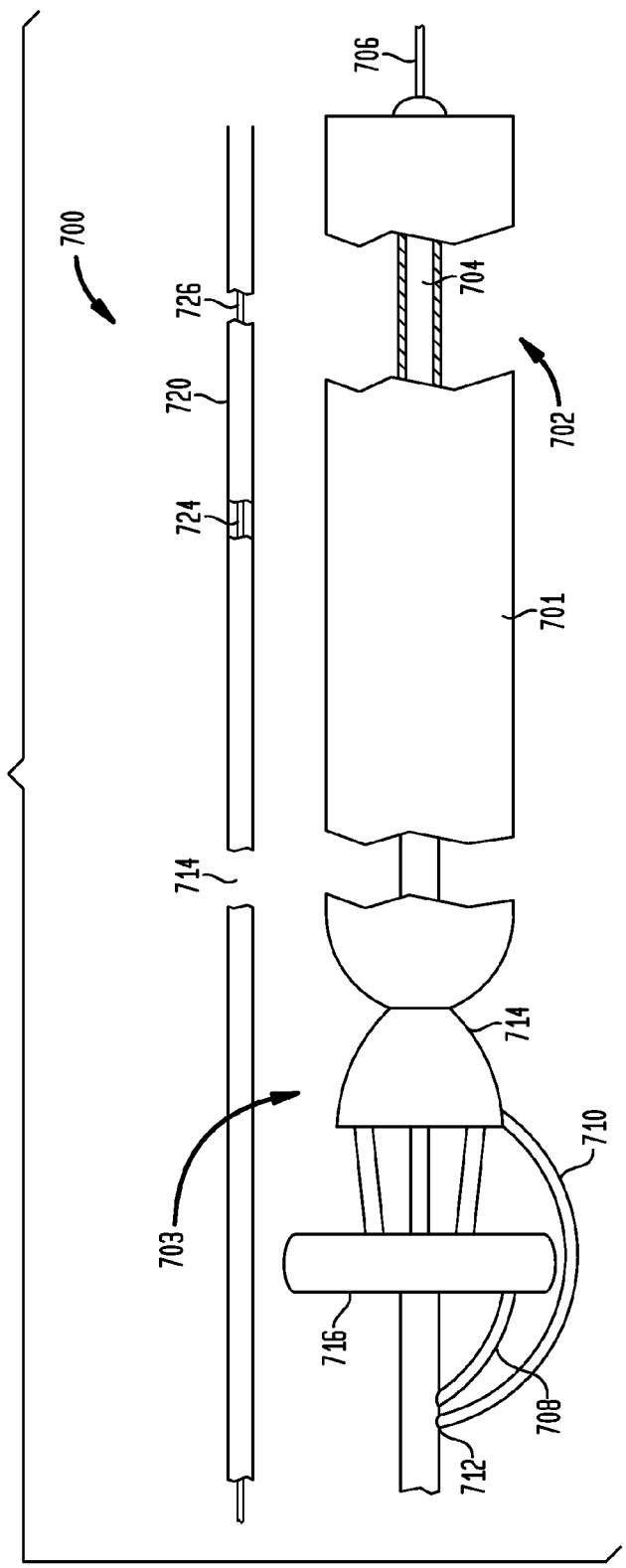
FIG. 25 illustrates a delivery system for implanting a bypass device in a patient according to one embodiment of the present invention.

FIG. 25 illustrates one embodiment of a delivery system 700 according to the present invention. As shown, delivery system 700 comprises a guidewire tube 702 configured for passing through a sleeve 701 of a bypass device 703 and having an internal lumen 704 for passage of a guidewire 706 (see FIGS. 26-31) and duodenal and gastric anchor inflation tubes 708, 710. Guidewire tube 702 further comprises an opening 712 to allow inflation tubes 708, 710 to pass out of the internal lumen 704 for coupling to valves (not shown) in duodenal and gastric anchors 714, 716. Opening 712 is also designed to for the release and removal of the inflation tubes from the duodenal and gastric anchors. As discussed above, pulling on the inflation tubes from outside of the patient will force opening 712 of guidewire tube 702 against the anchors and provide sufficient countertraction for the inflation tubes to disengage from the valves within the duodenal and gastric anchors.

Delivery system 700 further comprises a suture tube 720 having an internal lumen 722 for receiving a pull wire 724 and a series of openings 726 (only one opening 726 is shown for convenience in FIG. 25) for receiving suture (not shown). In use, a loop is formed in the suture and then passed through an opening 726. Pull wire 724 is then advanced distally such that it engages the suture loop and retains the suture loop within the lumen 722. The remaining ends of the suture may then be used to tie bypass device 703 to suture tube 720 and guidewire tube 702. In this manner, bypass device 730 may be tied to guidewire tube 702 at a series of points along its length such that the bypass device 730 can be advanced along with the guidewire 706 with guidewire tube 702 (discussed in detail below). Bypass device 730 is preferably tied such that sleeve 701 is crumpled around guidewire tube 702 and duodenal and gastric anchors 714, 716 are compressed in their uninflated configurations against guidewire 702. This facilitates advancement of bypass device 703 through the esophagus and pylorus of the patient. When bypass device 730 is in position within the patient, pull wire 724 is pulled distally out of the suture tube 720; thereby disengaging each of the suture loops and releasing bypass device from both suture tube 720 and guidewire tube 702.

Figure 26:
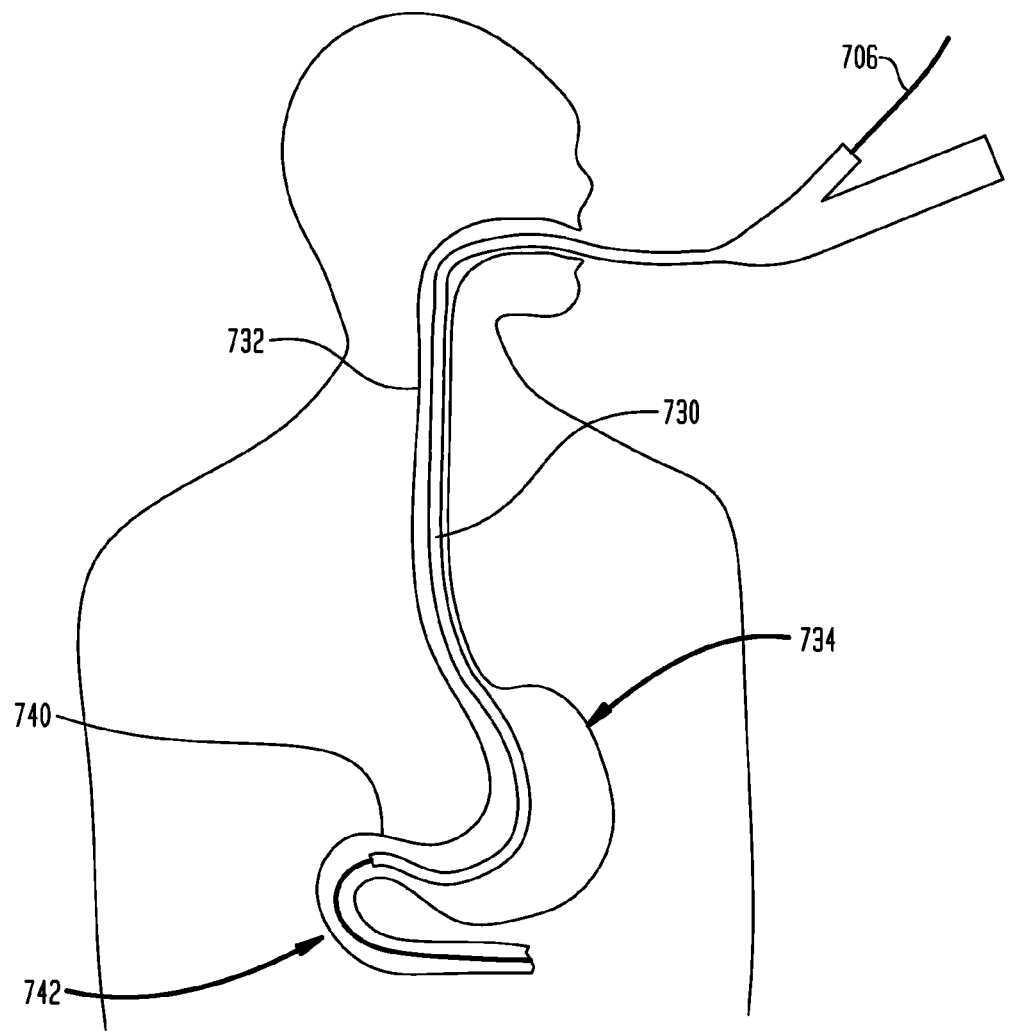
FIG. 26 illustrates a first step in a method for implanting a bypass device in a patient.

FIGS. 26-31 illustrate one embodiment of a method for implanting bypass device 703 into the patient. As shown in FIG. 26, the physician first advances an endoscope 730 through the patient's esophagus 732 and stomach 734 and into the small intestines 736. A guide wire 706 will then be advanced through the working channel of the endoscope 730 and into the small intestines 736. Preferably, the guide wire 706 is advanced to a position at least 12 inches into the small intestines and more preferably greater than 20 inches. This ensures that the guide wire will remain in place throughout the implantation process. The endoscope is then removed from the patient and the guide wire left in place.

Figure 27:
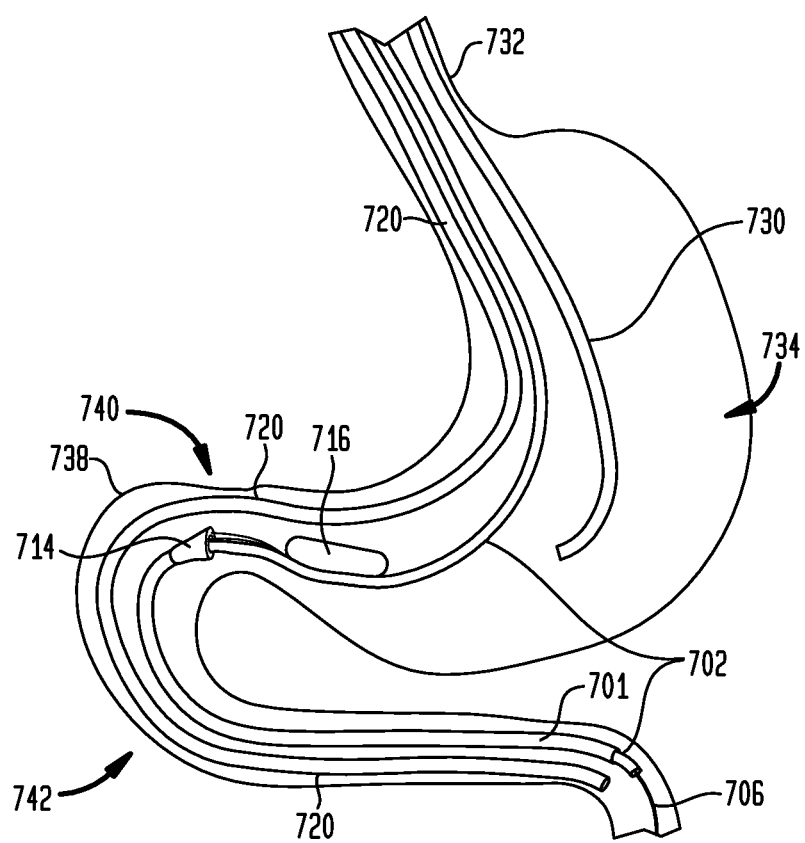
FIG. 27 illustrates the delivery system of FIG. 25 advancing along a guidewire within a stomach of the patient.

Referring now to FIG. 27, delivery system 700 and bypass device 703 are then positioned on guide wire 706 as discussed previously advanced along guide wire 706 until duodenal anchor 714 is positioned within the duodenal bulb 738 of the patient and gastric anchor 716 is generally positioned just proximal to pylorus 740. At this point, sleeve 701 will be fully extended through the duodenum 742 of the patient. The physician may advance scope 730 into stomach 734 to visualization the device and ensure that it is in the proper position.

Figure 28:
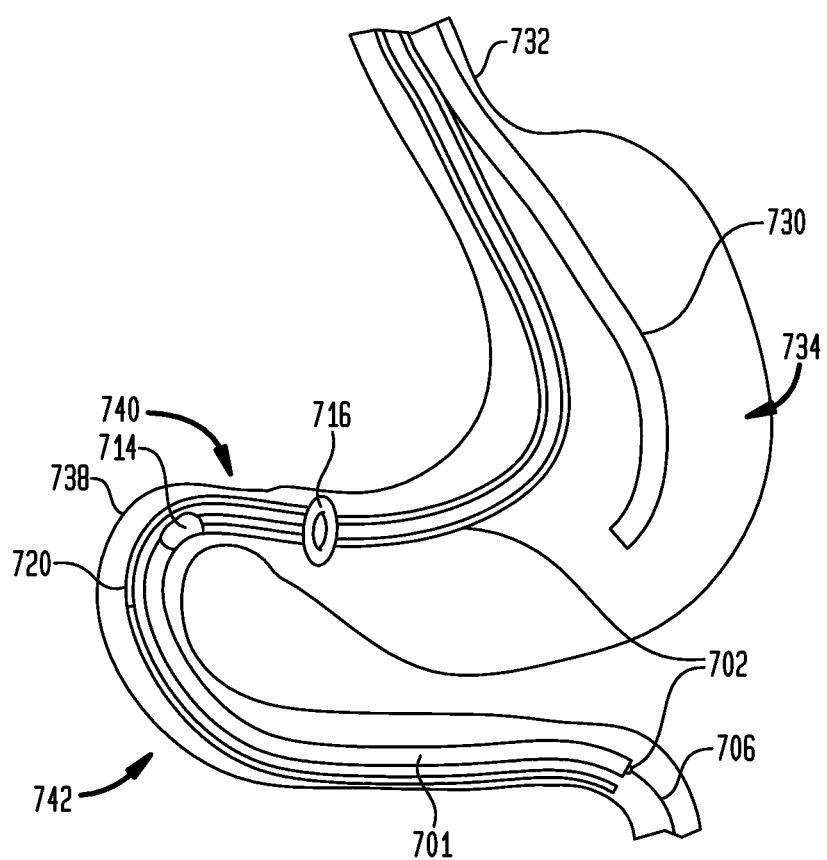
FIG. 28 illustrates the delivery system and the bypass device in position within the GI tract of the patient.

Referring now to FIG. 28, the physician may now withdraw pull wire 725 (see FIG. 25) from suture tube 720 to free the tied sutures and disengage bypass device 703 from both suture tube 720 and guide wire tube 702. When this occurs, sleeve 701 will naturally open up into its normal patent configuration and duodenal and gastric anchors 714, 716 will expand into their naturally uninflated configurations. Suture tube 720 may then be removed from the patient. In certain embodiments, the physician may extend a device (such as a snare or the like) through scope 730 to assist with the removal of suture tube 720.

Figure 29:
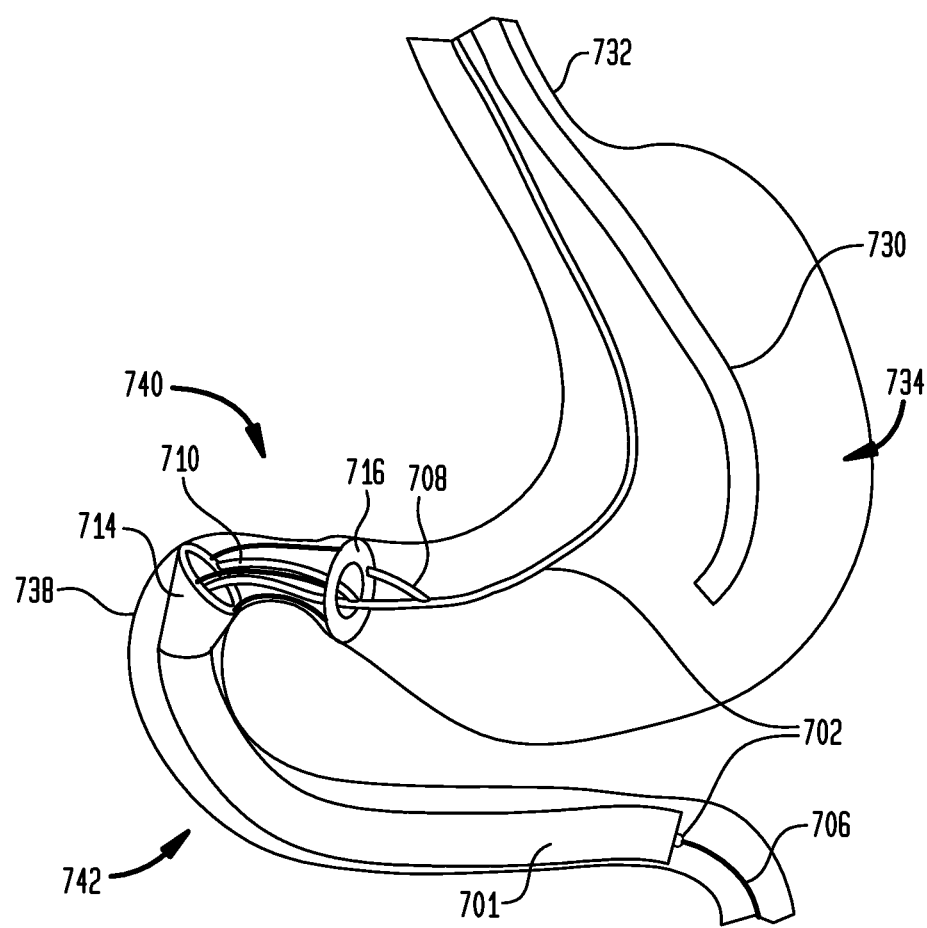
FIG. 29 illustrates the inflation of the duodenal and gastric anchors according to the method of the present invention.

As shown in FIG. 29, physician then inflates the anchors 714 and 716 by delivering fluid through inflation tubes 708 and 710. Once the anchors have expanded to the appropriate size (typically about 15-30 ml of fluid in the gastric anchor 716 and about 7-10 ml of fluid in the duodenal anchor), the physician pulls on inflation tubes 708, 710 to disengage them from the valves in the gastric and duodenal anchors. The inflation tubes may then be withdrawn from the patient.

Figure 30:
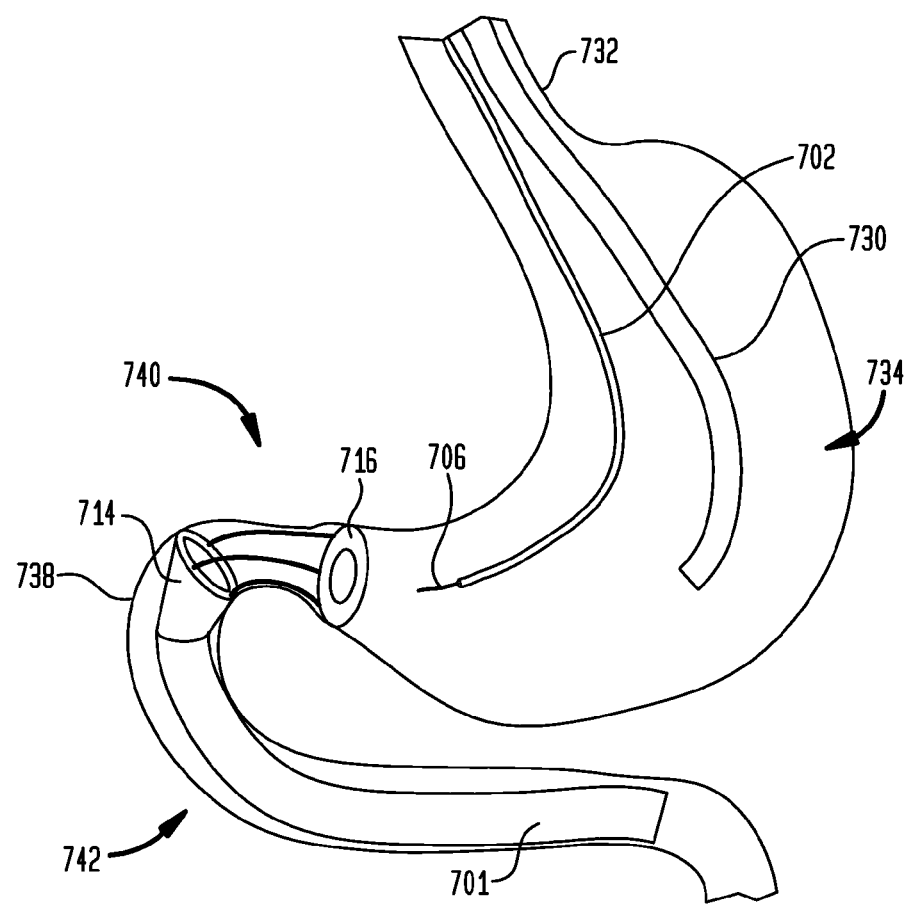
FIG. 30 illustrates the removal of the guidewire tube according to the method of the present invention.
Figure 31:
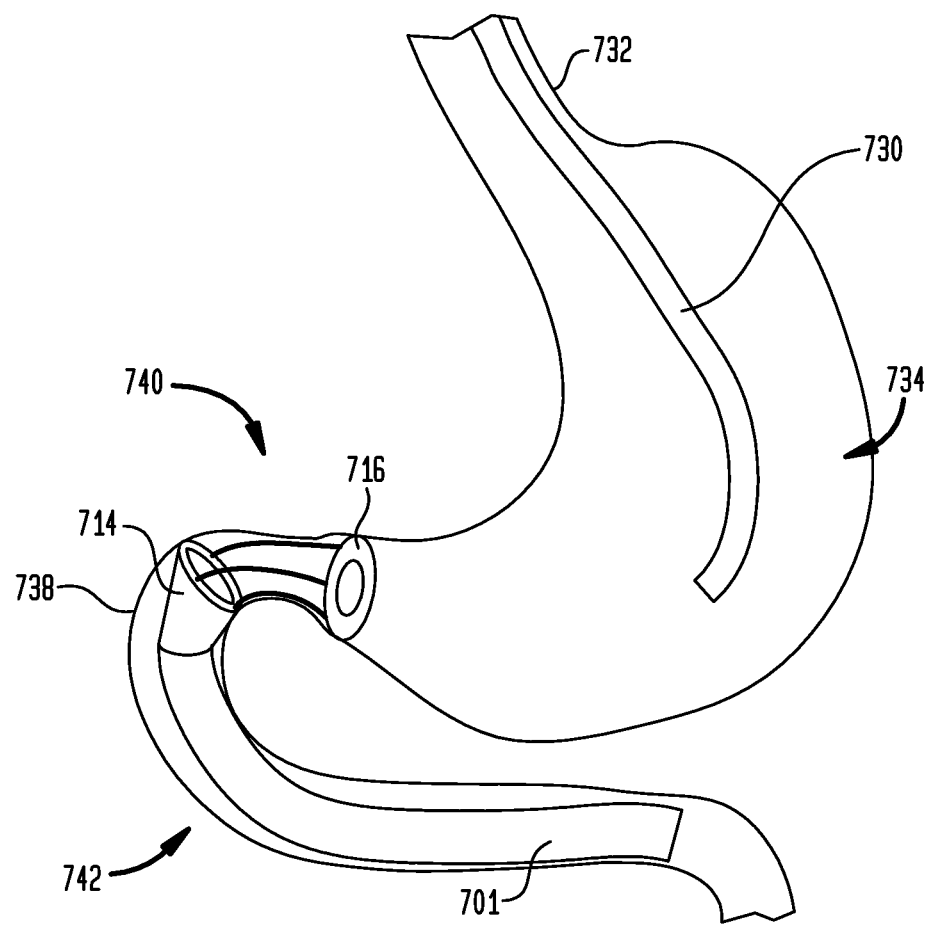
FIG. 31 illustrates the bypass device in its final implanted position within the patient according to the method of the present invention.

As shown in FIGS. 30 and 31, the physician then withdraws guide wire tube 702 and guide wire 706 from the patient and bypass device 703 has been implanted. Scope 730 may be used to visualize final placement of the device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a patient for obesity and/or type II diabetes comprising:
    positioning a duodenal anchor within a proximal portion of a duodenum of the patient, the anchor comprising an internal tube with an outer wall and an expandable element coupled to the outer wall;
    securing the duodenal anchor within the proximal portion of the duodenum with a rib element surrounding a portion of the internal tube, the rib element being housed within an interior of the expandable element to provide rigidity to the internal tube; and
    coupling a flexible tube member such that the flexible tube member extends through at least a portion of the duodenum of the patient.

2. The method of claim 1 wherein the securing step further comprises expanding the expandable element to a size that exceeds the maximally dilated size of a human pylorus.

3. The method of claim 1 wherein the internal tube has a longitudinal axis and has a length in the longitudinal axis that is longer than a diameter of the internal tube.

4. The method of claim 1 wherein the expandable element comprises an inflatable balloon having proximal and distal end portions and wherein the proximal end portion has a larger diameter in an inflated configuration than the distal end portion.

5. The method of claim 1 wherein the flexible tube member is coupled to a distal end of the internal tube.

6. The method of claim 1 wherein the flexible tube member has open proximal and distal ends and has a length of about 3-12 inches.

7. The method of claim 1 further comprising the steps of positioning a gastric anchor in a stomach antrum and coupling the gastric anchor to the duodenal anchor to inhibit distal migration of the duodenal anchor.

8. The method of claim 7 wherein the coupling step is carried out by coupling one or more flexible tethers to the duodenal and gastric anchors across a pylorus of the patient.

9. The method of claim 1 wherein the expandable element tapers inward from the proximal end portion to the distal end portion.

10. A method for treating a patient for obesity and/or type II diabetes comprising:
    positioning a duodenal anchor within a proximal portion of a duodenum of the patient, the anchor comprising a support member having open proximal and distal ends and a biasing member coupled to the support member;
    securing the duodenal anchor within the proximal portion of the duodenum by exerting an outwardly directed force with the biasing member against the support member; and
    coupling a flexible tube member such that the flexible tube member extends through at least a portion of the duodenum of the patient.

11. The method of claim 10 device wherein the proximal end of the support member has a larger diameter than the distal end of the support member.

12. The method of claim 10 wherein the support member has a funnel shape.

13. The method of claim 10 wherein the biasing member comprises a spring enclosed within the support member.

14. The method of claim 10 wherein the duodenal anchor comprises a shape memory material configured to expand to a configuration that exerts a force against the inner walls of the duodenum.

15. The method of claim 10 wherein the flexible tube member is coupled to a distal end of the internal tube.

16. The method of claim 10 wherein the flexible tube member has open proximal and distal ends and has a length of about 3-12 inches.

17. The method of claim 10 further comprising the steps of positioning a gastric anchor in a stomach antrum and coupling the gastric anchor to the duodenal anchor to inhibit distal migration of the duodenal anchor.

18. The method of claim 17 wherein the coupling step is carried out by coupling one or more flexible tethers to the duodenal and gastric anchors across a pylorus of the patient.

* * * * *